United States Patent [19]

Melloni et al.

[11] 4,271,160

[45] Jun. 2, 1981

[54] SUBSTITUTED MORPHOLINE DERIVATIVES AND PHARMACEUTICAL COMPOSITIONS

[75] Inventors: Piero Melloni, Bresso; Arturo Della Torre, Gallarate; Giovanni C. Carniel; Alessandro Rossi, both of Milan, all of Italy

[73] Assignee: Farmitalia Carlo Erba S.p.A., Milan, Italy

[21] Appl. No.: 161,509

[22] Filed: Jun. 20, 1980

Related U.S. Application Data

[62] Division of Ser. No. 1,604, Jan., 1979, Pat. No. 4,229,449.

[30] Foreign Application Priority Data

| Jan. 20, 1978 | [IT] | Italy | 19449 A/78 |
| Jan. 20, 1978 | [IT] | Italy | 19450 A/78 |
| Dec. 5, 1978 | [IT] | Italy | 30533 A/78 |
| Dec. 5, 1978 | [IT] | Italy | 30534 A/78 |
| Dec. 5, 1978 | [IT] | Italy | 30535 A/78 |

[51] Int. Cl.$^3$ .................. A61K 31/535; C07D 265/30
[52] U.S. Cl. ..................... 424/248.54; 424/248.56; 424/248.58; 544/148; 544/165; 544/167
[58] Field of Search ............... 544/148, 165, 167; 424/248.54, 248.56, 248.58

[56] References Cited

U.S. PATENT DOCUMENTS

| 3,974,158 | 8/1976 | Young ........................ 544/165 |
| 4,016,284 | 4/1977 | Vanhoof et al. .............. 544/148 |

*Primary Examiner*—Henry R. Jiles
*Assistant Examiner*—R. W. Ramsuer
*Attorney, Agent, or Firm*—Murray and Whisenhunt

[57] ABSTRACT

Substituted morpholine derivatives, such as, for instance the compound 2-[α-(3,4-methylendioxy-phenoxy)-benzyl]-morpholine are disclosed.

The claimed compounds are active on the central nervous system, and may be used as antidepressant agents.

8 Claims, No Drawings

SUBSTITUTED MORPHOLINE DERIVATIVES AND PHARMACEUTICAL COMPOSITIONS

This is a divisional application of Ser. No. 1,604, filed Jan. 8, 1979 now U.S. Pat. No. 4,229,449.

The present invention relates to substituted propanolamine and morpholine derivatives, to a process for their preparation and to pharmaceutical compositions containing them.

The compounds covered by this invention have the general formula (I)

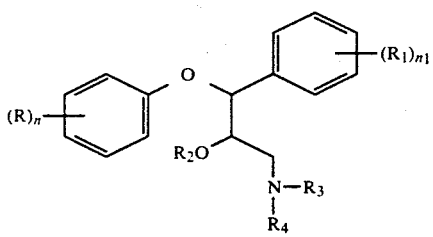

(I)

wherein
n and $n_1$ are, independently, 1, 2 or 3;
each or the groups R and $R_1$, which may be the same or different, is hydrogen; halogen; halo-$C_1$-$C_6$alkyl; hydroxy; $C_1$-$C_6$alkoxy; $C_1$-$C_6$alkyl optionally substituted; aryl-$C_1$-$C_6$alkyl optionally substituted; aryl-$C_1$-$C_6$alkoxy optionally substituted; —$NO_2$;

wherein $R_5$ and $R_6$ are, independently, hydrogen or $C_1$-$C_6$ alkyl, or two adjacent R groups or two adjacent $R_1$ groups, taken together, form the —O—$CH_2$—O— radical;
$R_2$ is hydrogen; $C_1$-$C_{12}$alkyl optionally substituted, or aryl-$C_1$-$C_6$alkyl;
each of the groups $R_3$ and $R_4$, which may be identical or different, is hydrogen, $C_1$-$C_6$alkyl optionally substituted, $C_2$-$C_4$alkenyl, $C_2$-$C_4$alkynyl, aryl-$C_1$-$C_4$alkyl optionally substituted, $C_3$-$C_7$cycloalkyl optionally substituted, or $R_3$ and $R_4$ with the nitrogen atom to which they are bounded form a pentatomic or hexatomic saturated or unsaturated, optionally substituted, heteromonocyclic radical optionally containing other heteroatoms belonging to the class of O, S and N;
or $R_2$ and $R_4$, taken together, form the —$CH_2$—$CH_2$— radical.

This invention also includes the pharmaceutically acceptable salts of compounds with formula (I) as well as all the possible isomers and their mixtures, the metabolites provided with pharmacological, e.g. antidepressant, activity and the metabolic precursors of the compounds with formula (I).

The alkyl, alkenyl, alkynyl and alkoxy groups may be straight or branched chains.

When one or more of the groups R and $R_1$ is a substituted $C_1$-$C_6$ alkyl group, it is preferably $C_1$-$C_6$ alkyl substituted by one or more substituents chosen from hydroxy, $C_1$-$C_6$ alkoxy,

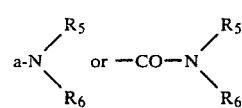

group, in which $R_5$ and $R_6$ are as defined above.
An aryl group is preferably phenyl.

When one or more of the groups $R_3$ and $R_4$ is a substituted $C_1$-$C_6$ alkyl group it is preferably $C_1$-$C_6$ alkyl substituted by one or more substituents chosen from halogen, hydroxy, $C_1$-$C_6$ alkoxy,

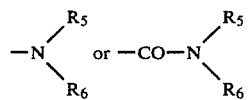

with $R_5$ and $R_6$ as defined above. The same substituents may be present on a substituted $C_1$-$C_{12}$ alkyl group.

Substituted aryl-$C_1$-$C_6$alkyl, aryl-$C_1$-$C_4$alkyl and aryl-$C_1$-$C_6$alkoxy groups are preferably aryl-$C_1$-$C_6$alkyl, aryl-$C_1$-$C_4$alkyl and aryl-$C_1$-$C_6$alkoxy groups in which the aryl group is substituted by one or more $C_1$-$C_6$alkyl, halogen, halo-$C_1$-$C_6$alkyl, hydroxy, $C_1$-$C_6$alkoxy and

with $R_5$ and $R_6$ as defined above.

A substituted $C_3$-$C_7$cycloalkyl group is a $C_3$-$C_7$cycloalkyl substituted by one or more substituents preferably chosen from $C_1$-$C_6$alkyl, halogen, halo-$C_1$-$C_6$alkyl, hydroxy, $C_1$-$C_6$alkoxy and

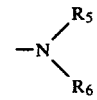

in which $R_5$ and $R_6$ are as defined above.

A $C_1$-$C_6$alkyl group is preferably methyl, ethyl or isopropyl.

A $C_1$-$C_{12}$alkyl group is preferably methyl, ethyl, isopropyl or octyl.

A $C_2$-$C_4$ alkenyl group is preferably vinyl or allyl.
A $C_2$-$C_4$alkynyl group is preferably propargyl.
A halo-$C_1$-$C_6$alkyl group is preferably trihalo-$C_1$-$C_6$alkyl, in particular trifluoromethyl.
A $C_1$-$C_6$alkoxy group is preferably methoxy or ethoxy.
An aryl-$C_1$-$C_6$alkyl or aryl-$C_1$-$C_4$alkyl group is preferably benzyl or phenethyl.
An aryl-$C_1$-$C_6$ alkoxy group is preferably benzyloxy.
In a

group, $R_5$ and $R_6$ preferably are, independently, hydrogen or $C_1$-$C_3$ alkyl, in particular methyl, ethyl or isopropyl.

A C$_3$–C$_7$cycloalkyl group is preferably cyclopropyl, cyclopentyl or cyclohexyl. When R$_3$ and R$_4$, with the nitrogen atom to which they are linked, form a substituted heteromonocyclic radical, the substituents are preferably C$_1$–C$_6$alkyl or aryl, in particular methyl or phenyl; preferred heteromonocyclic radicals are morpholino, piperidino, N-pyrrolidinyl, N-methyl-piperazinyl and N-phenyl-piperazinyl.

When two adjacent R groups or two adjacent R$_1$ groups form the —O—CH$_2$—O— radical, this is preferably a 3,4-methylendioxy radical.

Owing to the presence of at least two asymmetric carbon atoms, for each compound of formula (I) at least two distinct diastereoisomers may exist, from which at least four distinct enantiomers may be obtained: both the single diastereoisomers and their mixture as well as the single enantiomers are included in the object of this invention.

Examples of pharmaceutically acceptable salts of compounds (I) are both the salts with inorganic acids, for example hydrochloric acid, hydrobromic acid, sulphuric acid, and the salts with organic acids, for example, citric acid, tartaric acid, methansulphonic acid, fumaric acid, malic acid, maleic acid and mandelic acid.

According to this invention preferred salts of compounds (I) are those in which the

group is salified with one of the acids mentioned above, preferably the hydrochloric acid.

Preferred compounds of the invention are the compounds with formula (I) wherein n and n$_1$ are independently 1 or 2; each of the groups R and R$_1$ is, independently, hydrogen, methoxy, ethoxy, chlorine, trifluoromethyl or two adjacent R groups form a —O—CH$_2$—O— radical; R$_2$ is hydrogen or methyl; one of the groups R$_3$ and R$_4$ is hydrogen and the other is methyl as well as the pharmaceutically acceptable salts thereof.

Particularly preferred compounds of the invention are the compounds with formula (I) wherein n and n$_1$ are, independently 1 or 2; each of the groups R and R$_1$ is, independently, hydrogen, methoxy, ethoxy, chlorine, trifluoromethyl or two adjacent R groups form the radical —O—CH$_2$—O—; R$_2$ and R$_4$, taken together, form the radical —CH$_2$—CH$_2$—, R$_3$ is hydrogen, methyl or isopropyl as well as the pharmaceutically acceptable salts thereof.

Examples of compounds preferred under this invention are:
2-(α-phenoxy-benzyl)-morpholine;
2-[α-(2-methoxy-phenoxy)-benzyl]-morpholine;
2-[α-(3-methoxy-phenoxy)-benzyl]-morpholine;
2-[α-(4-methoxy-phenoxy)-benzyl]-morpholine;
2-[α-(2-ethoxy-phenoxy)-benzyl]-morpholine;
2-[α-(4-chloro-phenoxy)-benzyl]-morpholine;
2-[α-(3,4-methylendioxy-phenoxy)-benzyl]-morpholine;
2-[α-(2-methoxy-phenoxy)-2-methoxy-benzyl]-morpholine;
2-[α-(2-ethoxy-phenoxy)-2-methoxy-benzyl]-morpholine;
2-[α-(2-ethoxy-phenoxy)-4-ethoxy-benzyl]-morpholine;
2-[α-(4-chloro-phenoxy)-4-ethoxy-benzyl]-morpholine;
2-[α-(2-methoxy-phenoxy)-4-ethoxy-benzyl]-morpholine;
2-[α-(2-methoxy-phenoxy)-2-chloro-benzyl]-morpholine;
2-[α-(2-ethoxy-phenoxy)-2-chloro-benzyl]-morpholine;
2-[α-(2-methoxy-phenoxy)-3-chloro-benzyl]-morpholine;
2-[α-(2-ethoxy-phenoxy)-3-chloro-benzyl]-morpholine;
2-[α-(2-ethoxy-phenoxy)-4-chloro-benzyl]-morpholine;
2-[α-(2-methoxy-phenoxy)-4-chloro-benzyl]-morpholine;
2-[α-(2-methoxy-phenoxy)-4-trifluoromethyl-benzyl]-morpholine;
2-[α-(4-ethoxy-phenoxy)-4-trifluoromethyl-benzyl]-morpholine;
2-[α-(2-methoxy-phenoxy)-3,4-dichloro-benzyl]-morpholine;
2-[α-(2-ethoxy-phenoxy)-3,4-dichloro-benzyl]-morpholine;
4-methyl-2-[α-(2-methoxy-phenoxy)-benzyl]-morpholine;
4-methyl-2-[α-(2-ethoxy-phenoxy)-benzyl]-morpholine;
4-methyl-2-[α-(2-methoxy-phenoxy)-3-chloro-benzyl]-morpholine;
4-methyl-2-[α-(2-ethoxy-phenoxy)-3-chloro-benzyl]-morpholine;
4-methyl-2-[α-(2-ethoxy-phenoxy)-4-chloro-benzyl]-morpholine;
4-methyl-2-[α-(2-methoxy-phenoxy)-4-chloro-benzyl]-morpholine;
4-methyl-2-[α-(2-methoxy-phenoxy)-4-trifluoromethyl-benzyl]-morpholine;
4-methyl-2-[α-(2-ethoxy-phenoxy)-4-trifluoromethyl-benzyl]-morpholine;
4-isopropyl-2-[α-(2-methoxy-phenoxy)-benzyl]-morpholine;
4-isopropyl-2-[α-(2-ethoxy-phenoxy)-benzyl]-morpholine;
4-isopropyl-2-[α-(2-methoxy-phenoxy)-3-chloro-benzyl]-morpholine;
4-isopropyl-2-[α-(2-ethoxy-phenoxy)-3-chloro-benzyl]-morpholine;
4-isopropyl-2-[α-(2-ethoxy-phenoxy)-4-chloro-benzyl]-morpholine;
4-isopropyl-2-[α-(2-methoxy-phenoxy)-4-chloro-benzyl]-morpholine;
4-isopropyl-2-[α-(2-methoxy-phenoxy)-4-trifluoromethyl-benzyl]-morpholine;
4-isopropyl-2-[α-(2-ethoxy-phenoxy)-4-trifluoromethyl-benzyl]-morpholine;
N-methyl-2-hydroxy-3-phenoxy-3-phenyl-propylamine;
N-methyl-2-hydroxy-3-(2-methoxy-phenoxy)-3-phenyl-propylamine;
N-methyl-2-hydroxy-3-(2-ethoxy-phenoxy)-3-phenyl-propylamine;
N-methyl-2-hydroxy-3-(4-chloro-phenoxy)-3-phenyl-propylamine;
N-methyl-2-hydroxy-3-(3,4-methylenedioxy-phenoxy)-3-phenyl-propylamine;
N-methyl-2-hydroxy-3-(2-methoxy-phenoxy)-3-(2-chloro-phenyl)-propylamine;
N-methyl-2-hydroxy-3-(2-ethoxy-phenoxy)-3-(2-chloro-phenyl)-propylamine;
N-methyl-2-hydroxy-3-(2-methoxy-phenoxy)-3-(3-chloro-phenyl)-propylamine;
N-methyl-2-hydroxy-3-(2-ethoxy-phenoxy)-3-(3-chloro-phenyl)-propylamine;

N-methyl-2-hydroxy-3-(2-methoxy-phenoxy)-3-(4-chloro-phenyl)-propylamine;
N-methyl-2-hydroxy-3-(2-ethoxy-phenoxy)-3-(4-chloro-phenyl)-propylamine;
N-methyl-2-hydroxy-3-(2-methoxy-phenoxy)-3-(4-trifluoromethyl-phenyl)-propylamine;
N-methyl-2-hydroxy-3-(2-ethoxy-phenoxy)-3-(4-trifluoromethyl-phenyl)-propylamine;
N-methyl-2-hydroxy-3-(2-methoxy-phenoxy)-3-(3,4-dichloro-phenyl)-propylamine;
N-methyl-2-hydroxy-3-(2-ethoxy-phenoxy)-3-(3,4-dichloro-phenyl)-propylamine;
N-methyl-2-methoxy-3-phenoxy-3-phenyl-propylamine;
N-methyl-2-methoxy-3-(2-methoxy-phenoxy)-3-phenyl-propylamine;
N-methyl-2-methoxy-3-(2-ethoxy-phenoxy)-3-phenyl-propylamine;
N-methyl-2-methoxy-3-(4-chloro-phenoxy)-3-phenyl-propylamine;
N-methyl-2-methoxy-3-(3,4-methylendioxy-phenoxy)-3-phenyl-propylamine;
N-methyl-2-methoxy-3-phenoxy-3-(2-chloro-phenyl)-propylamine;
N-methyl-2-methoxy-3-(2-methoxy-phenoxy)-3-(2-chloro-phenyl)-propylamine;
N-methyl-2-methoxy-3-(2-ethoxy-phenoxy)-3-(2-chloro-phenyl)-propylamine;
N-methyl-2-methoxy-3-(2-methoxy-phenoxy)-3-(3-chloro-phenyl)-propylamine;
N-methyl-2-methoxy-3-(2-ethoxy-phenoxy)-3-(3-chloro-phenyl)-propylamine;
N-methyl-2-methoxy-3-(2-methoxy-phenoxy)-3-(4-chloro-phenyl)-propylamine;
N-methyl-2-methoxy-3-(2-ethoxy-phenoxy)-3-(4-chloro-phenyl)-propylamine;
N-methyl-2-methoxy-3-(2-methoxy-phenoxy)-3-(4-trifluoromethyl-phenyl)-propylamine;
N-methyl-2-methoxy-3-(2-ethoxy-phenoxy)-3-(4-trifluoromethyl-phenyl)-propylamine;
N-methyl-2-methoxy-3-(2-methoxy-phenoxy)-3-(3,4-dichloro-phenyl)-propylamine; N-methyl-2-methoxy-3-(2-ethoxy-phenoxy)-3-(3,4-dichloro-phenyl)-propylamine, as well as their pharmaceutically acceptable salts.

The compounds of the invention are prepared by a process comprising:

(a) reducing a compound of formula (II)

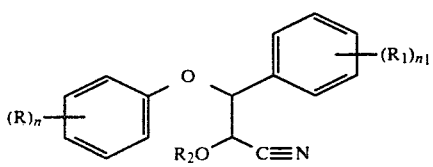

(II)

wherein n, $n_1$, R, $R_1$ and $R_2$ are as defined above, so obtaining compounds of formula (I) wherein $R_3$ and $R_4$ are both hydrogen and R, $R_1$, n, $n_1$ and $R_2$ are as defined above; or (b) reducing a compound of formula (III)

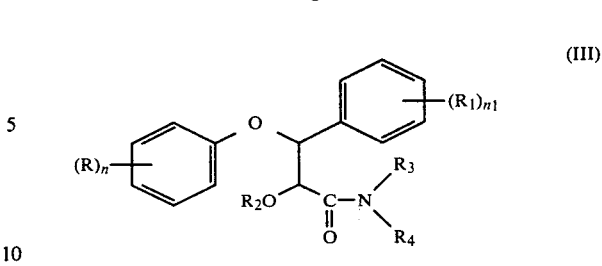

(III)

wherein n, $n_1$, R, $R_1$, $R_2$, $R_3$ and $R_4$ have the meanings reported above; or (c) reducing a compound of formula (IV)

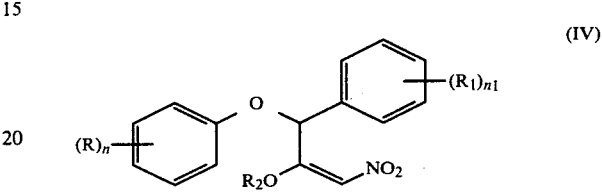

(IV)

wherein n, $n_1$ and $R_2$ are as defined above and R and $R_1$ have the meanings reported above except —$NO_2$, or a salt thereof, so obtaining compounds of formula (I) wherein n, $n_1$ and $R_2$ are as defined above, R and $R_1$ have the meanings reported above except —$NO_2$, and $R_3$ and $R_4$ are both hydrogen; or (d) reacting a compound of formula (V)

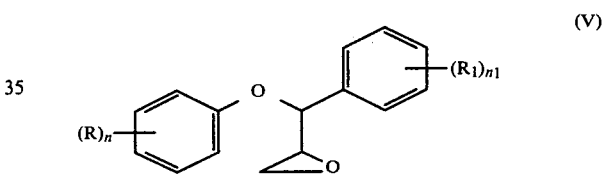

(V)

wherein n, $n_1$, R and $R_1$ are as defined above, with an amine of formula $HNR_3R_4$ in which $R_3$ and $R_4$ are as defined above, so obtaining compounds with formula (I) wherein $R_2$ is hydrogen, n, $n_1$, R, $R_1$, $R_3$ and $R_4$ have the meanings reported above, except the meaning of $R_4$ as forming, together with $R_2$, the radical —$CH_2$—$CH_2$—; or (e) reducing a compound of formula (VI)

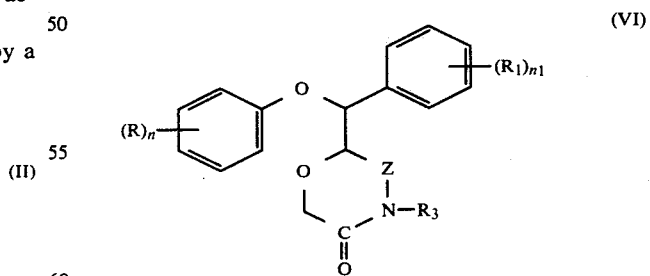

(VI)

wherein n, $n_1$, R, $R_1$ and $R_3$ are as defined above, and Z is >$CH_2$ or >C=O, so obtaining compounds of formula (I) wherein $R_2$ and $R_4$, taken together, form the radical —$CH_2$—$CH_2$— and n, $n_1$, R, $R_1$ and $R_3$ are as defined above; or (f) reductively cyclizing a compound of formula (VII)

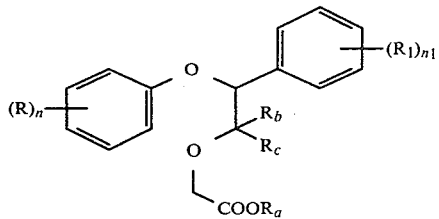
(VII)

wherein n, n₁, R and R₁ are as defined above, $R_a$ is $C_1$-$C_6$-alkyl, one of $R_b$ and $R_c$ is hydrogen and the other is —C≡N or $R_b$ and $R_c$, taken together, form the radical =CH—NO₂, so obtaining compounds of formula (I) wherein n, n₁, R and R₁ are as defined above, R₂ and R₄, taken together, form the radical —CH₂—CH₂— and R₃ is hydrogen; or (g) cyclizing a compound of formula (VIII)

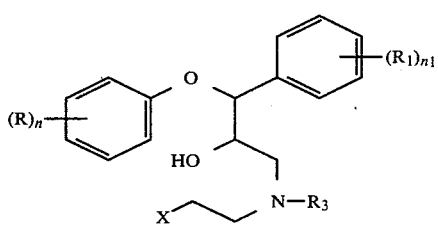
(VIII)

wherein n, n₁, R, R₁ and R₃ are as defined above and X is hydroxy or halogen or the residue of a reactive ester of an alcohol, so obtaining compounds of formula (I) wherein R₂ and R₄, taken together, form the radical —CH₂—CH₂— and n, n₁, R, R₁ and R₃ are as defined above; or (h) reacting a compound of formula (IX)

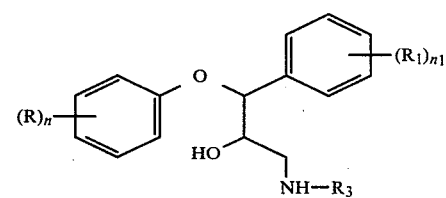
(IX)

wherein n, n₁, R, R₁ and R₃ are as defined above, with a compound of formula (X)

Y—CH₂—CH₂—Y (X)

wherein each of the groups Y, whether the same or different, is halogen or the residue of a reactive ester of an alcohol, so obtaining compounds of formula (I) wherein R₂ and R₄, taken together, form the radical —CH₂—CH₂— and n, n₁, R, R₁ and R₃ are as defined above and, if desired, converting a compound with formula (I) into another compound with formula (I) and/or, if desired, salifying a compound with formula (I) or obtaining a free compound from a salt and/or, if desired, resolving a mixture of isomers into the individual isomers.

The reduction of a compound of formula (II) as well as the reduction of a compound of formula (III) may be, in general, effected by the methods usually employed for the reduction of nitriles and amides, for example by treatment with LiAlH₄ or BH₃ in an inert anhydrous solvent, preferably an aliphatic ether, e.g. diethyl ether, or tetrahydrofuran, or a mixture of these solvents at temperatures varying from about 0° C. to solvent reflux temperature, or by treatment with an alkaline boronhydride, e.g. NaBH₄, in the presence of alkaline metals as described, for example, in Tetr. Lett. 1969, page 4555. Alternatively the reduction of a compound of formula (II) may be carried out by catalytic hydrogenation using, e.g., Raney nickel or Pd/C as catalyst and operating in the presence of liquid ammonia in a solvent which may be, for example, a $C_1$-$C_6$-aliphatic alcohol, e.g. methanol or ethanol, or the water at atmospheric pressure and at temperatures ranging from room temperature to about 50° C.

A salt of a compound of formula (IV) is, for example, the salt of a compound of formula (IV) in which R₂ is hydrogen with an alkaline metal, e.g. sodium or potassium: this salt can be obtained directly in the course of the preparation of the compound (IV) described later.

The reduction of a compound of formula (IV) or a salt thereof may be performed by conventional way, for example with LiAlH₄ as described, e.g., in J. Org. Chem. 39, page 2852 (1974) or with sodium bis-(2-metoxyetoxy)aluminiumdihydride, i.e. NaAlH₂(OC₂H₄OCH₃)₂, as reported, e.g., in Chem. Comm. 1974, page 307. The reaction of a compound of formula (V) with an amine of formula HNR₃R₄ may be effected by known methods, preferably without solvents but also in the presence of a solvent such as, for example, an aqueous or aqueous-alcoholic solvent or dimethylformamide, operating, if necessary, in a stopped vessel, at temperatures ranging from room temperature to approximately 150° C.

The reduction of a compound of formula (VI) may be performed by the same method reported above for the reduction of a compound of formula (III) using, for example, the procedure described in J. Med. Chem., vol 19, page 41 (1976), particularly when Z, in the compound (VI), represents a group >C=O.

The reductive cyclization of a compound of formula (VII) may be carried out by treatment with a suitable reducing agent by known procedures, preferably with BH₃ in an inert anhydrous solvent, e.g. an aliphatic ether, for example diethylether, or tetrahydrofuran, at temperatures varying preferably between about 0° C. and about 40° C.

When in the compound of formula (VIII) X is halogen this is preferably chlorine or bromine, when X is the residue of a reactive ester of an alcohol, it is preferably —O—mesyl or —O—tosyl.

The cyclization of a compound of formula (VIII) may be effected by conventional way, for example, when X is hydroxy, by boiling in a solvent able to form an azeotropic mixture with water, e.g. toluene, in the presence of an acid catalyst, e.g. p-toluensulphonic acid or BF₃ and/or in the presence of a dehydrating agent, e.g. anhydrous CuSO₄; or 3 when X is halogen or the residue of a reactive ester of an alcohol, by treatment with a base, for example with potassium tert. butylate in tert. butyl alcohol or with sodium hydride in dimethylformamide, dimethylsulphoxyde or dimethylacetamide, or with butyl lithium or lithium diisopropylamine and similar in tetrahydrofuran or in an aliphatic ether, e.g. diethylether, or with NaNH₂ or KNH₂ in ammonia using the procedures known in the organic chemistry.

When in the compound of formula (VIII) one or more of the substituents R and R₁ represents an hydroxy group, in order to avoid that this group interfere in the cyclization reaction, an amount of base sufficient to salify all the hydroxy groups present is preferably employed: the reactivity of the alcoholic salified hydroxy group is higher than that of the salified phenolic hydroxy group which therefore does not interfere in the reaction.

In a compound of formula (X) preferably the groups Y are both halogen, and in this case preferably one of them is chlorine and the other is iodine, or they are both —O—tosyl, or, preferably, they are both —O—mesyl.

The reaction of a compound of formula (IX) with a compound of formula (X) wherein the groups Y are both halogen, in particular with 1-chloro-2-iodo-ethane, may be performed, for example, using equimolecular amounts of the reagents in presence of an amount at least equimolecular of a strong base preferably chosen from the group of the alkaline hydrides, e.g. sodium hydride, or of a small excess of an alkaline or alkaline-earth carbonate or bicarbonate, e.g. $Na_2CO_3$, $K_2CO_3$ or $NaHCO_3$. The used solvent preferably is a polar solvent, for example dimethylformamide, and the reaction temperature may vary from room temperature to solvent reflux temperature, preferably arounding 50° C.

The reaction of a compound of formula (IX) with a compound of formula (X) wherein both the groups Y represent the residue of a reactive ester of an alcohol, in particular —O—mesyl, may be carried out by treating, under cooling, the mixture containing equimolecular amounts of the reagents in an apolar solvent, e.g. benzene or an aliphatic ether, for example diethylether, with at least two molar equivalents of a strong base such as, for example, butyl lithium, lithium isopropylamide or sodium amide in ammonia.

The interference in the reaction between compounds (IX) and compounds (X) of the hydroxy groups in case represented by the substituents R and $R_1$ can be avoided using an excess of the base analogously to what reported above in connection with the cyclization of a compound of formula (VIII).

When in the compounds having the formulae (II), (III), (IV), (VI) and (VII) reported above one or more of the substituents R, $R_1$, $R_3$ and $R_4$ represent reducible groups and we wish to maintain these groups unchanged in the final compounds (I), then the reductions reported above at the points (a), (b), (c), (e) and (f) are preferably performed using selective conditions.

Thus, for example, the reduction of compounds with formula (II), (III), (VI) and (VII) containing groups halogen or nitro may be effected selectively as to these groups operating, for example, with $BH_3$ in tetrahydrofuran or an aliphatic ether, e.g. diethylether, under nitrogen atmosphere, for example according to the procedure described in J. Am. Chem. Soc. 86, 3566 (1964) or also with Zn in ethanol as described in Experientia 33 (I), 101–102 (1977). The reduction of a compound of formula (IV) wherein one or more of the groups R and $R_1$ is halogen may be carried out selectively as to the halogen using, e.g., Red-Al, i.e. $NaAlH_2(OC_2H_4OCH_3)_2$, as reducing agent. The reduction of compounds of formula (III) and (VI) wherein $R_3$ or $R_4$ is $C_2$–$C_4$ alkenyl or $C_2$–$C_4$ alkynyl may be carried out selectively as to these groups using, e.g., $LiAlH_4$ in the reaction conditions previously reported. However, in these conditions $NO_2$-groups and halogen atoms, in case present, are reduced too, therefore compounds (I) wherein one or more of the substituents R and $R_1$ represents a nitro group or a halogen atom and $R_3$ represents, at the same time, $C_2$–$C_4$-alkenyl or $C_2$–$C_4$-alkynyl cannot be prepared by the reduction processes reported above. These compounds may be obtained, for example, by the processes indicated above at the points (d), (g) or (h) or by conversion of a compound of formula (I) into another compound of formula (I).

The same considerations apply to the other reductive processes described in the present application either whether they regard the preparation of final compounds or whether they regard the preparation of intermediate compounds. Both the optional conversion of a compound of formula (I) into another compound of formula (I) and the optional salification or the preparation of a free compound of formula (I) from a salt thereof as well as the optional resolution of a mixture of isomers can be effected by conventional way.

For example, a compound of formula (I) wherein $R_3$ is hydrogen and $R_4$ has the meanings reported above or, together with $R_2$, form a group —$CH_2$—$CH_2$— may be converted into the corresponding compound of formula (I) wherein $R_3$ is $C_1$–$C_6$-alkyl, $C_2$–$C_4$ alkenyl, $C_2$–$C_4$ alkynyl, aryl-$C_1$–$C_4$ alkyl or $C_3$–$C_7$ cycloalkyl by the usual methods of alkylation of the amines for example the reductive amination or the mere alkylation.

The reductive amination consists in reacting a compound of formula (I) wherein $R_3$ and/or $R_4$ is hydrogen with the suitable carbonyl compound, that is aldehyde or ketone, in the presence of a reducing agent which may be the hydrogen or, preferably, a mixed hydride, e.g. $NaBH_3CN$ or $NaBH_4$, or the formic acid according to the Leuckart-Wallach reaction.

When the reducing agent is the hydrogen the reductive amination is preferably carried out in an alcoholic solvent, e.g. methanol or ethanol, in the presence of a catalyst such as, e.g., Raney nickel or Pd/C at atmospheric pressure and at temperature varying from room temperature to about 50° C. according to the procedure described, e.g., in Org. Reactions, 4, 174 (1948). When the reducing agent is a mixed hydride, e.g. $NaBH_3CN$ or $NaBH_4$, the reductive amination may be effected in the presence of an excess of the hydride operating preferably at room temperature according to the methods described in Tetr. Lett., 3, 261 (1963), J. Org. Chem., 37, 1673 (1972), Synthesis, 3, 140 (1975). When the reductive amination is carried out with the formic acid according to the Leuckart-Wallach reaction, the formic acid may be present in excess and the reaction mixture may be preferably heated for a time varying from two to twelve hours as described, e.g., in Org. Reactions, 5, 301 (1949).

The alkylation reaction may be performed, for example, by treatment with the appropriate alkyl or aralkyl halide or with a reactive ester, e.g. tosylate or mesylate, of the appropriate alcohol. The alkylation may be carried out either in the absence of solvents or in a solvent such as, e.g., water, an aliphatic alcohol, e.g. ethyl or methyl alcohol, a glycol, e.g. ethylenic or propylenic glycol, benzene or dimethylformamide or a mixture of these solvents in the presence of an acid acceptor such as, for example, triethylamine, an alkaline carbonate or bicarbonate or an excess of the amine, at temperatures ranging from about 60° C. to solvent reflux temperature according to the procedures described, e.g., in J. Org. Chem. 2, 139 (1938); Org. Synt. Coll., vol. II, 183 (1943); J. Amer. Chem. Soc., 54, 4457 (1932).

The monoalkylation may be effected, alternatively, by the methods described for example in J. Org. Chem.

40, 23, 3453 (1975); J. Chem. Soc. c 2223 (1969); J. Med. Chem. 17 (1), 654 (1974).

The conversion of a compound of formula (I) wherein one of $R_3$ and $R_4$ is hydrogen into the corresponding compound of formula (I) wherein one of $R_3$ and $R_4$ is methyl may be carried out in particular, also be reaction with ethyl chloroformiate in chloroform, in the presence of an excess of KOH at a temperature ranging from about 0° C. to about 5° C. and by reduction of the obtained carbamic ester with an excess of $LiAlH_4$ or $BH_3$ in anhydrous diethylether at the reflux temperature.

A compound of formula (I) wherein one of $R_3$ and $R_4$ is $C_1$-$C_6$ alkyl and the other is hydrogen may be obtained, alternatively: (a') reacting a compound of formula (I) wherein both $R_3$ and $R_4$ are hydrogen with benzaldehyde in a solvent such as, e.g., benzene or toluene at the reflux temperature; (b') reducing the obtained Schiff base, for example by catalytic hydrogenation in an alcoholic solvent in the presence of Raney nickel or Pd/C, or with mixed hydrides, e.g. $LiAlH_4$ or $NaBH_4$, as described, for example, in Houben-Weyl, vol. XI, part 1, page 341 (1957); (c') alkylating the obtained benzylamine with the appropriate alkyl halide by the alkylation procedure previously described and finally (d') removing the benzyl group, for example by catalytic hydrogenation, according to the procedure described in J. Amer. Chem. Soc. 63, 1964 (1941), or, preferably, by treatment with ethyl chloroformiate at the reflux temperature according to the method described in J. Med. Chem. 18(6), 576 (1975). By proceding analogously a compound of formula (I) where one of $R_3$ and $R_4$ is benzyl may be converted into the corresponding compound of formula (I) wherein one of $R_3$ and $R_4$ is hydrogen. A compound of formula (I) where $R_3$ and $R_4$ are both hydrogen may be converted into the corresponding compound of formula (I) wherein one of $R_3$ and $R_4$ is hydrogen and the other is benzyl by reaction with benzoyl chloride in the presence of aqueous sodium hydroxyde in an organic solvent such as, e.g., dichloromethane preferably at temperatures varying from 0° C. to room temperature and then reducing the obtained benzoylamino derivative with a mixed hydride, e.g. $LiAlH_4$ or $BH_3$ in tetrahydrofuran or diethylether at the solvent reflux temperature.

A compound of formula (I) wherein $R_2$ is hydrogen may be converted into a compound of formula (I) wherein $R_2$ is $C_1$-$C_{12}$ alkyl or aryl-$C_1$-$C_6$ alkyl by the methods usually employed for the etherification of the alcohols, for example reacting an alkaline salt of the alcohol, e.g. the lithium or the sodium salt, with the appropriate alkyl or aralkyl halide; the reaction may be carried out at a temperature varying from the room to the reflux temperature in an organic solvent which may be, for example, the same solvent wherein the alkaline salt of the alcohol was prepared.

The lithium salt of the alcohol may be obtained by reaction with a lithium alkyl, e.g., lithium butyl, in an inert anhydrous solvent such as, e.g., tetrahydrofuran; the sodium salt may be obtained by reaction with sodium metal or sodium hydride in an inert anhydrous solvent such as, e.g., benzene, toluene or dimethylformamide. By analogous way a compound of formula (I) where one of the groups R and $R_1$ is hydroxy may be converted into the corresponding compound of formula (I) where one of the groups R and $R_1$ is $C_1$-$C_6$ alkoxy or aryl-$C_1$-$C_6$ alkoxy.

A compound of formula (I) where $R_2$ is $C_1$-$C_6$ alkoxy or aryl-$C_1$-$C_6$ alkoxy may be converted into the corresponding compound of formula (I) where $R_2$ is hydroxy by the usual methods of de-etherification; for example a compound of formula (I) where $R_2$ is methoxy may be de-etherified by treatment with pyridine hydrochloride or with boron tribromide or with $C_2H_5$ SK in dimethylformamide at 100°-130° C. as described, e.g., in J. Med. Chem. 20(1), 165 (1977). When the de-etherification is carried out with piridine hydrochloride it is preferably performed under nitrogen atmosphere at temperatures arounding 150° C. The de-etherification with boron tribromide is preferably carried out by adding to a solution of the compound of formula (I), cooled at a temperature between $-70°$ and $-80°$ C., a solution of $BBr_3$ in chloroform operating under nitrogen atmosphere and terminating the reaction at 0° C. by addition of methyl alcohol.

A compound of formula (I) where $R_3$ and $R_4$ are both methyl may be converted into the corresponding compound of formula (I) where one of $R_3$ and $R_4$ is methyl and the other is hydrogen, for example, by treatment with ethyl chloroformiate in benzene or toluene at the solvent reflux temperature and by subsequent treatment with alcoholic KOH at the reflux temperature.

A compound of formula (I) where one of the substituents R and $R_1$ is a group $—NO_2$ may be converted into the corresponding compound of formula (I) wherein one of the groups R and $R_1$ is $—NH_2$ by the methods usually employed for the reduction of the aromatic nitro-derivatives, for example by catalytic hydrogenation using, e.g., platinum, palladium or Raney nickel as catalyst according to the known procedures of the organic chemistry.

A compound of formula (I) where one of the substituents R and $R_1$ is amino may be transformed into the corresponding compound of formula (I) where one of the groups R and $R_1$ is hydroxy, converting the amine into the corresponding diazonium salt and then hydrolysing this for example according to the procedure described in Org. Synth. 23, 11 (1943), or as described in J. Org. Chem. 42, 2053 (1977).

A compound of formula (I) where one of the groups R and $R_1$ is amino may be converted into the corresponding compound of formula (I) wherein one of the groups R and $R_1$ is mono- or di-$C_1$-$C_6$ alkylamino by reductive amination or by alkylation as previously reported. As stated above also the salification of a compound of formula (I) as well as the preparation of a free compound from its salt and the separation of the isomers from a mixture may be effected in a conventional manner.

Thus, for example, the salt of a compound of formula (I) with hydrochloric acid may be obtained by treatment with anhydrous gaseous hydrochloric acid or an anhydrous alcoholic solution of hydrochloric acid in an anhydrous solvent such as, e.g., diethylether, benzene, ethyl alcohol and isolating the hydrochloride by filtration or evaporation of the solvent.

The separation of the isomers, e.g. diastereoisomers, from their mixture may be performed by fractionate cristallization from a suitable solvent or by chromatography.

The chromatographic separation may be carried out both by thin layer preparative chromatography and by column chromatography using silica gel or magnesium silicate as support and, e.g., benzene, ethyl acetate, cyclohexane, chloroform, methylene chloride, ethyl ether or their mixtures as elution solvents, or by HPLC.

The optional conversions reported above for the compounds of formula (I) as well as the separation of the isomers, e.g. diastereoisomers, from a mixture may also be effected, if desired, on the starting materials or on the intermediate compounds.

The compounds of formula (II) where $R_2$ is hydrogen may be prepared from the aldehydes of formula (XI)

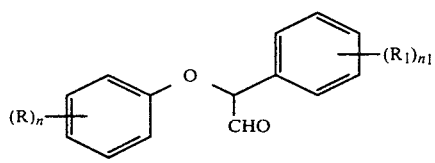
(XI)

where R, $R_1$, n and $n_1$ are as defined above, by the methods usually employed for converting the aldehydes into cyanohydrins, for example by treatment with a metabisulfite, preferably an alkaline, e.g. sodium, metabisulfite in the presence of a cyanide preferably an alkaline, e.g. sodium or potassium, cyanide, operating in a suitable solvent such as, e.g., diethylenglycol dimethylether, water, an aliphatic alcohol, e.g. ethyl alcohol, or a mixture of these solvents, at temperatures ranging from room temperature to about 100° C., preferably from 50° C. to about 90° C.

The compounds of formula (II) where $R_2$ is $C_1$-$C_{12}$ alkyl optionally substituted or aryl-$C_1$-$C_6$ alkyl may be obtained by etherification of the compounds of formula (II) where $R_2$ is hydrogen according to the conventional procedures, e.g. by treating the alkaline salt of the alcohol with the appropriate alkyl or aralkyl halide as previously reported for the analogous conversions on compounds of formula (I). The compounds of formula (III) wherein $R_2$, $R_3$ and $R_4$ have the meanings reported above except the meaning of $R_2$ and $R_4$ as forming, taken together, —$CH_2$—$CH_2$—, may be prepared by the usual methods of preparation of the amides, for example by reacting an amine of formula $HNR_3R_4$ where $R_3$ and $R_4$ are as defined above, with a compound of formula (XII)

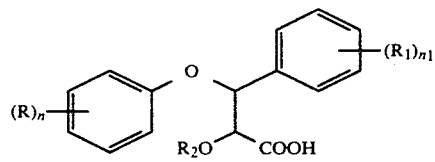
(XII)

where R, $R_1$, n, $n_1$ and $R_2$ are as defined above, or, preferably, with a reactive derivative thereof, for example an acid halide or a $C_1$-$C_6$-alkyl-, preferably ethyl-, ester. The reaction may be carried out either in the absence of solvent or in the presence of a suitable solvent such as, e.g., a $C_1$-$C_6$ aliphatic alcohol, for example ethyl alcohol, in the presence, if necessary, of a condensing agent, e.g. dicyclohexyl carbodiimide, or of an acid acceptor, for example an alkaline carbonate or bicarbonate or a tertiary amine, e.g. triethylamine, or an excess of the amine of formula $HNR_3R_4$.

The compounds of formula (III) wherein $R_2$ and $R_4$, taken together, form the radical —$CH_2$—$CH_2$— may be prepared, for example, by cyclizing a compound of formula (XIII)

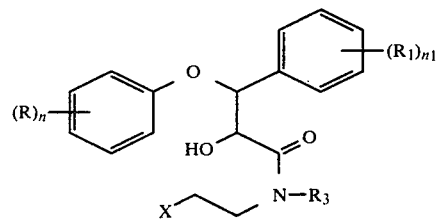
(XIII)

where R, $R_1$, n, $n_1$ and $R_3$ have the meanings reported above and X is hydroxy or halogen or, preferably, the residue of a reactive ester of an alcohol, e.g. a tosylate or a mesylate, operating for example, in the reaction conditions reported above for the cyclization of a compound of formula (VIII), preferably, when X is halogen or the residue of a reactive ester of an alcohol, in the presence of an amount at least equimolecular of a base preferably chosen from the group of the alkaline carbonates and bicarbonates, e.g. $K_2CO_3$, in a suitable solvent, e.g. dimethylformamide, dimethylsulphoxyde and similar.

Compounds of formula (III) wherein $R_2$ and $R_4$, taken together, form the radical —$CH_2$—$CH_2$— may be also obtained, alternatively, from a compound of formula (XIV)

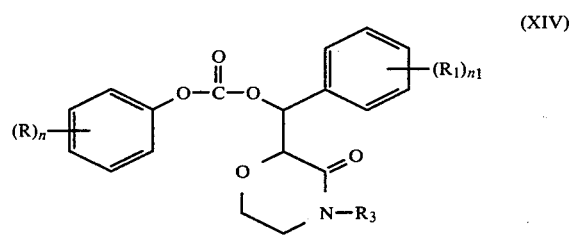
(XIV)

where R, $R_1$, n, $n_1$ and $R_3$ are as defined above, by heating at temperatures ranging from about 120° to about 180° C. in an appropriate solvent such as, e.g., hexamethylenphosphortriamide, as described, for example in Can. J. Chem. 49, 914 (1971).

The compounds of formula (IV) may be prepared by treating, for example, a reactive derivative of the compound of formula (XII), which may be, for instance, one of the reactive derivatives indicated above or, preferably, the amide obtained by reacting the acid of formula (XII) with carbonyldiimidazole, with nitromethane in the presence of a base such as, e.g. an alkaline hydride, for example sodium hydride, in an appropriate anhydrous solvent, e.g. tetrahydrofuran. In this way compounds of formula (IV) in which $R_2$ is the cation of the used base are obtained, which, if desired, may be etherified by conventional methods, for example as reported above, to give compounds of formula (IV) where $R_2$ is $C_1$-$C_{12}$ alkyl optionally substituted or aryl-$C_1$-$C_6$ alkyl, or acidified to give the ketonic form of the compounds of formula (IV) where $R_2$ is hydrogen.

The compounds of formula (V) may be prepared by known methods, for example oxidizing a compound of formula (XV)

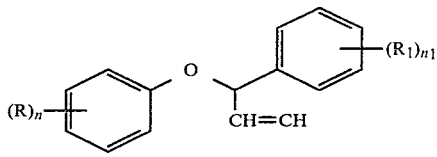

(XV)

where R, $R_1$, n and $n_1$ are as defined above, for example with a peroxy acid, preferably m-chloro-perbenzoic acid, in an organic solvent, e.g. dichloromethane, chloroform, benzene or acetone, or according to the method described in Tetrahedron 28, 3009 (1972) from the aldehydes of formula (XI).

The compounds of formula (VI) wherein Z is >$CH_2$ may be prepared, for example, by cyclizing a compound of formula (XVI)

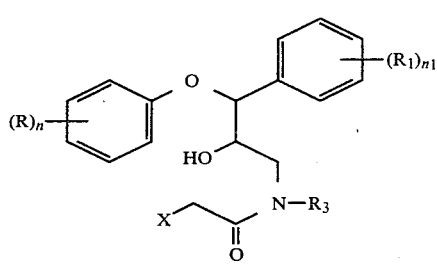

(XVI)

where R, $R_1$, n, $n_1$, $R_3$ and X have the meanings reported above, using approximately the same reaction conditions reported above for the cyclization of a compound of formula (VIII).

The compounds of formula (VI) wherein Z is >C=O may be obtained, for example, by reacting a compound of formula (XVII)

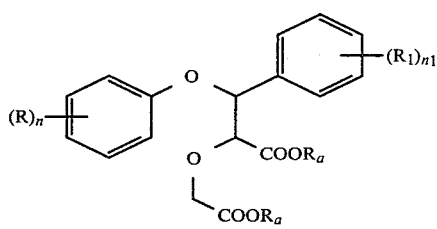

(XVII)

where R, $R_1$, n, $n_1$ are as defined above and each of the groups $R_a$, which may be identical or different, is $C_1$-$C_6$ alkyl, preferably methyl or ethyl, with an amine of formula $R_3$—$NH_2$ where $R_3$ has the meanings reported above. The reaction is preferably carried out under pressure in a suitable solvent, e.g. a $C_1$-$C_6$ aliphatic alcohol, for example ethyl alcohol, at temperatures varying from about 50° to about 150° C. If the reaction is performed using controlled temperature, time and stoichiometry conditions, then a compound of formula (XVII) where one of the groups —$COOR_a$ is replaced by a group —$CONHR_3$ is obtained, from which a compound of formula (VI) may be obtained by boiling, e.g. in acetic acid, or by treatment with a strong base, e.g. NaH, in a suitable solvent, e.g. dimethylformamide or dimethylsulphoxide. Compounds (VI) may also be obtained from the imides corresponding to the amides of formula (XIV) by the same procedure described above for the preparation of compounds (III) from compounds (XIV).

The compounds of formula (VII) where one of the groups $R_b$ and $R_c$ is hydrogen and the other is —C≡N may be prepared by known methods, for example by reacting a compound of formula (II) wherein $R_2$ is hydrogen with a $C_1$-$C_6$ alkyl-halo-acetate, for example ethylbromoacetate, in the presence of a base, e.g. an alkaline carbonate or bicarbonate, e.g. $K_2CO_3$, in an anhydrous solvent such as, for example, dimethylacetamide, diemthylformamide, dimethylsulphoxide and similar at temperatures varying, e.g., from room temperature to about 80° C.

The compounds of formula (VII) where $R_b$ and $R_c$, taken together, form the radical =CH—$NO_2$ may be obtained, by analogous way, starting from a compound of formula (IV) wherein $R_2$ is a cation, e.g. an alkaline cation, for example sodium, by reaction with a $C_1$-$C_6$ alkyl-halo-acetate, preferably ethylbromoacetate, at temperatures ranging from about 0° C. to about 50° C. in an anhydrous solvent such as, for example, tetrahydrofuran, dioxane or one of the solvents hereabove mentioned.

The compounds of formula (VIII) may be prepared, for instance, from the compounds of formula (IX) as described, e.g. in Ind. J. Chem. 13, 462 (1975), or by reducing a compound of formula (XVI) using the known methods of the organic chemistry, for example with $BH_3$ under nitrogen atmosphere at a temperature between about −10° C. and about 0° C. in an inert anhydrous solvent such as, e.g., tetrahydrofuran or an aliphatic ether, e.g. diethylether.

The compounds of formula (IX) where $R_3$ is hydrogen may be prepared by the methods indicated previously at the points (a), (b) and (c). The compounds of formula (IX) where $R_3$ is different from hydrogen may be obtained alkylating by known methods, e.g. those reported above for the alkylation of the amines, the compounds of formula (IX) where $R_3$ is hydrogen, or reducing the compounds of formula (III) wherein $R_2$ is hydrogen as described above.

The compounds of formula (X) are known compounds or, respectively, may be prepared by known methods.

The aldehydes of formula (XI) may be obtained by the usual methods for preparing the aldehydes described in the Organic Chemistry, e.g. oxidizing the corresponding primary alcohols, e.g. by treatment with 99% phosphoric acid in the presence of dicyclohexylcarbodiimide by conventional way, or reducing the corresponding acid chlorides according to known procedures. This reduction may be performed, e.g., with a mixed hydride, in particular with tri-tert.butoxy lithium aluminium hydride, at temperatures varying between about −70° C. and about −50° C. in an anhydrous solvent, for example diethylenglycol dimethylether, tetrahydrofuran, diethylether and similar. The acid chlorides mentioned above may be in turn obtained from the corresponding carboxylic acids, that is α-phenoxyphenyl acetic acids, by the classic methods of the organic chemistry, for example by treatment with thionyl chloride or with oxalyl chloride in the absence of solvents or in an organic anhydrous solvent, e.g. benzene, toluene and similar, according to known procedures.

The compounds of formula (XII), as well as the reactive derivatives of the compounds of formula (XII), may be prepared by known methods; in particular the $C_1$–$C_6$ alkyl esters of the compounds of formula (XII) where $R_2$ is hydrogen may be obtained, e.g., reacting a compound of formula (XVIII)

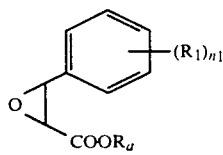 (XVIII)

where $R_1$, $n_1$ and $R_a$ have the meanings reported above, with a compound of formula (XIX)

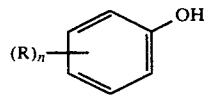 (XIX)

where R and n are as defined above, in the presence of a catalytic amount of a base which may be, for instance, an alkaline, e.g. sodium, carbonate or a strong base or the salt of the phenol of formula (XIX), either in the absence of solvents or in an appropriate solvent, e.g. a $C_1$–$C_6$ aliphatic alcohol, preferably ethyl alcohol, or dimethylformamide.

The compounds of formula (XIII) may be prepared, for example, by treating a reactive derivative of a compound of formula (XII) where $R_2$ is hydrogen, preferably a $C_1$–$C_6$ alkyl ester thereof, with a compound of formula HO—$CH_2$—$NHR_3$, wherein $R_3$ is as defined above and, if desired, converting the compound of formula (XIII) where X is —OH, so obtained, into the corresponding halide or reactive ester by known methods.

The compounds of formula (XIV) may be prepared by known methods, for example by treating a compound of formula (XX)

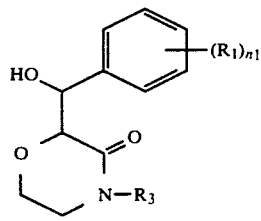 (XX)

where $R_1$, $n_1$ and $R_3$ are as defined above, with the appropriate phenyl chloroformiate in the presence of a base, e.g. pyridine, by standard procedures.

The compounds of formula (XVI) may be obtained, for example, by reacting a compound of formula (IX) with a compound of formula

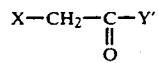

where X has the meanings reported above and Y' is halogen, preferably chlorine, by known methods, for instance in an organic or aqueous-organic solvent, e.g. methylenchloride or methylenchloride and water, in presence of a base, e.g. NaOH.

The compounds of formula (XVII) may be prepared from a compound of formula (XII) where $R_2$ is hydrogen and the carboxy group is esterified as a $C_1$–$C_6$ alkyl ester, by treatment with a $C_1$–$C_6$ alkyl-halo-acetate, preferably ethylbromoacetate, in presence of a base, e.g. $K_2CO_3$ or $Na_2CO_3$, in an appropriate solvent, e.g. dimethylformamide, by known methods.

The compounds of formula (XV), (XVIII), (XIX) and (XX) are known compounds or, respectively, may be prepared by known methods from known compounds. In particular, a compound of formula (XX) where $R_1$ is hydrogen, and $n_1$ is 1 may be obtained reacting the desired morpholin-3-one derivative with benzaldehyde in presence of a strong base, for example butyl lithium, in an anhydrous solvent, for example tetrahydrofuran, at a temperature varying between about $-70°$ C. and about $-50°$ C. By analogous way the compounds of formula (XX) where $R_1$ is different from hydrogen may be prepared.

The compounds of the present invention are active on the central nervous system, in particular, as antidepressant agents.

The antidepressant activity was evaluated in mice on the basis of the prevention of reserpine-induced blepharospasm and hypothermia. Reserpine was administered endoperitoneally at a dosage of 2.5 mg/kg, and the tested compounds were orally administered 30 minutes before the administration of reserpine. Recording of blepharospasm [evaluated in scores according to the technique described by Rubin B. et al. in J. Pharmacol., 120, 125 (1957)] and measurement of body temperature (by means of a rectal thermocouple) were taken an hour, and respectively four hours after the administration of reserpine.

The compounds of the present invention are preferably administered orally, although they can be administered also in other conventional ways, for example, by injection or by rectal way.

The dosage suitable for the oral administration to adult humans of the compounds of the invention, is preferably 5–30 mg pro dose 2–4 times a day.

The pharmaceutical compositions containing the compounds of the invention are prepared according to conventional methods with the usual ingredients.

Thus, for oral administration, the pharmaceutical compositions containing the compounds of the invention are preferably tablets, pills or capsules which contain the active substance together with diluents, such as, for example, lactose, dextrose, sucrose, mannitol, sorbitol, cellulose; lubricants, for instance, silica, talc, stearic acid, magnesium or calcium stearate and/or polyethylene glycols; or they may also contain binders, such as, for example, starches, gelatine, methylcellulose, gumarabic, tragacanth, polyvinylpyrrolidone; disintegrating agents, such as, for instance, starches, alginic acid, alginates; effervescing mixtures; dyestuffs; sweeteners; wetting agents, such as, for instance, lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

Also the other pharmaceutical formulations containing the compounds of the invention may be prepared by known methods and they can be, for example, syrups or drops for the oral administration, sterile solutions for injection, or suppositories.

In the following examples, THF, DMF, DMA, MCPBA and diglyme refer respectively to tetrahydrofuran, dimethylformamide, dimethylacetamide, m-chloro-perbenzoic acid and diethylenglycol dimethylether. Very broad melting points generally refer to mixtures of diastereoisomers.

The following examples illustrate but do not in any way limit the present invention.

EXAMPLE 1

To a well stirred mixture of 2-hydroxy-3-(3,4-methylendioxyphenoxy)-3-phenyl-propylamine (2.87 g) in CHCl$_3$ (28 ml), NaOH 2 N (8.3 ml) was added. The mixture was cooled to 0° C. and, at this temperature, over about 30', a solution of ethyl chloroformiate (1.58 ml) in CHCl$_3$ (2 ml) was dropped. The stirring was continued for 15', the organic phase was separated and the aqueous phase was extracted with CHCl$_3$. The combined organic extracts were washed with water, dried over Na$_2$SO$_4$ and evaporated to dryness to give N-ethoxy-carbonyl-2-hydroxy-3-(3,4-methylendioxyphenoxy)-3-phenyl-propylamine (oil; yield 94.8%).

This oil was dissolved in anhydrous diethylether (100 ml) and added dropwise, under stirring, to a mixture of LiAlH$_4$ (1.02 g) in anhydrous diethylether (25 ml).

The mixture was stirred at room temperature for 20 hours, cooled and decomposed with water (1 ml), 20% NaOH (0.75 ml) and water (3 ml). The residue was filtered off and washed with diethylether. The ether was dried over Na$_2$SO$_4$ and evaporated to dryness to give N-methyl-2-hydroxy-3-(3,4-methylendioxyphenoxy)-3-phenyl-propylamine, g 2.35; m.p. 100°–122° C. (yield 85%). Analogously, the following compounds were prepared:

N-methyl-2-hydroxy-3-phenoxy-3-phenyl-propylamine;
N-methyl-2-hydroxy-3-(2-methoxy-phenoxy)-3-phenyl-propylamine HCl m.p. 94°–112° C.
N-methyl-2-hydroxy-3-(3-methoxy-phenoxy)-3-phenyl-propylamine;
N-methyl-2-hydroxy-3-(4-methoxy-phenoxy)-3-phenyl-propylamine;
N-methyl-2-hydroxy-3-(2-ethoxy-phenoxy)-3-phenyl-propylamine;
N-methyl-2-hydroxy-3-(4-ethoxy-phenoxy)-3-phenyl-propylamine;
N-methyl-2-hydroxy-3-(2-chloro-phenoxy)-3-phenyl-propylamine;
N-methyl-2-hydroxy-3-(4-chloro)-phenoxy)-3-phenyl-propylamine;
N-methyl-2-hydroxy-3-(4-trifluoromethyl-phenoxy)-3-phenyl-propylamine;
N-methyl-2-hydroxy-3-phenoxy-3-(2-methoxy-phenyl)-propylamine;
N-methyl-2-hydroxy-3-(2-methoxy-phenoxy)-3-(2-methoxy-phenyl)-propylamine;
N-methyl-2-hydroxy-3-(2-ethoxy-phenoxy)-3-(2-methoxy-phenyl)-propylamine;
N-methyl-2-hydroxy-3-phenoxy-3-(4-ethoxy-phenyl)-propylamine;
N-methyl-2-hydroxy-3-(2-methoxy-phenoxy)-3-(4-ethoxy-phenyl)-propylamine;
N-methyl-2-hydroxy-3-(4-methoxy-phenoxy)-3-(4-ethoxy-phenyl)-propylamine;
N-methyl-2-hydroxy-3-(2-ethoxy-phenoxy)-3-(4-ethoxy-phenyl)-propylamine;
N-methyl-2-hydroxy-3-(4-ethoxy-phenoxy)-3-(4-ethoxy-phenyl)-propylamine;
N-methyl-2-hydroxy-3-(2-trifluoromethyl-phenoxy)-3-(4-ethoxy-phenyl)-propylamine;
N-methyl-2-hydroxy-3-(4-trifluoromethyl-phenoxy)-3-(4-ethoxy-phenyl)-propylamine;
N-methyl-2-hydroxy-3-phenoxy-3-(2-chloro-phenyl)-propylamine;
N-methyl-2-hydroxy-3-(2-methoxy-phenoxy)-3-(2-chloro-phenyl)-propylamine;
N-methyl-2-hydroxy-3-(2-ethoxy-phenoxy)-3-(2-chloro-phenyl)-propylamine;
N-methyl-2-hydroxy-3-phenoxy-3-(3-chloro-phenyl)-propylamine;
N-methyl-2-hydroxy-3-(2-methoxy-phenoxy)-3-(3-chloro-phenyl)-propylamine;
N-methyl-2-hydroxy-3-(2-ethoxy-phenoxy)-3-(3-chloro-phenyl)-propylamine;
N-methyl-2-hydroxy-3-phenoxy-3-(4-chloro-phenyl)-propylamine;
N-methyl-2-hydroxy-3-(2-methoxy-phenoxy)-3-(4-chloro-phenyl)-propylamine;
N-methyl-2-hydroxy-3-(2-ethoxy-phenoxy)-3-(4-chloro-phenyl)-propylamine;
N-methyl-2-hydroxy-3-phenoxy-3-(4-trifluoromethyl-phenyl)-propylamine;
N-methyl-2-hydroxy-3-(2-methoxy-phenoxy)-3-(4-trifluoromethyl-phenyl)-propylamine;
N-methyl-2-hydroxy-3-(4-methoxy-phenoxy)-3-(4-trifluoromethyl-phenyl)-propylamine;
N-methyl-2-hydroxy-3-(2-ethoxy-phenoxy)-3-(4-trifluoromethyl-phenyl)-propylamine;
N-methyl-2-hydroxy-3-(4-ethoxy-phenoxy)-3-(4-trifluoromethyl-phenyl)-propylamine;
N-methyl-2-hydroxy-3-phenoxy-3-(3,4-dichloro-phenyl)-propylamine;
N-methyl-2-hydroxy-3-(2-methoxy-phenoxy)-3-(3,4-dichloro-phenyl)-propylamine;
N-methyl-2-hydroxy-3-(2-ethoxy-phenoxy)-3-(3,4-dichloro-phenyl)-propylamine.

EXAMPLE 2

To a stirred solution of N-ethoxycarbonyl-2-hydroxy-3-(3,4-methylendioxy-phenoxy)-3-phenyl-propylamine (3.59 g) in anhydrous dimethylformamide (30 ml) and methyliodide (6.23 ml) cooled to 0°–5° C., 55% NaH (4.36 g) was added. Stirring and cooling were continued for 1 hour and 30'.

The reaction mixture was cautiously decomposed with water then diluted with plentiful water and extracted with ethyl acetate; the organic phase was washed with water, dried over Na$_2$SO$_4$ and evaporated to dryness.

The residue was purified by dissolving it in methanol and filtering off the insoluble material. The filtrate was evaporated to dryness to give N-methyl-N-ethoxycarbonyl-2-methoxy-3-(3,4-methylendioxy-phenoxy)-3-phenyl-propylamine, 3.1 g; oil; yield 80.2%.

The obtained oil was heated to the reflux temperature, under stirring, with 10% methanolic KOH (44.8 ml). After 48 hours, the reaction mixture was concentrated to dryness then n-propyl alcohol was added to reintegrate the original volume. The whole was boiled for 20 hours and evaporated to dryness; the residue was taken up with water and extracted with diethylether. The ether was extracted with 3% HCl, the acidic extract was basified with 20% NaOH and re-extracted with diethylether. The organic phase was washed with water, dried over Na$_2$SO$_4$ and evaporated to dryness to give N-methyl-2-methoxy-3-(3,4-methylendioxyphenoxy)-3-phenyl-propylamine, 2.05 g; oil; yield 81.3%. HCl m.p. 142°–145° C.

Analogously the following compounds were prepared:

N-methyl-2-methoxy-3-phenoxy-3-phenyl-propylamine;
N-methyl-2-methoxy-3-(2-methoxy-phenoxy)-3-phenyl-propylamine. HCl m.p. 115°–120° C.
N-methyl-2-methoxy-3-(3-methoxy-phenoxy)-3-phenyl-propylamine;
N-methyl-2-methoxy-3-(4-methoxy-phenoxy)-3-phenyl-propylamine;
N-methyl-2-methoxy-3-(2-ethoxy-phenoxy)-3-phenyl-propylamine;
N-methyl-2-methoxy-3-(4-ethoxy-phenoxy)-3-phenyl-propylamine;
N-methyl-2-methoxy-3-(2-chloro-phenoxy)-3-phenyl-propylamine;
N-methyl-2-methoxy-3-(4-chloro-phenoxy)-3-phenyl-propylamine;
N-methyl-2-methoxy-3-(4-trifluoromethyl-phenoxy)-3-phenyl-propylamine;
N-methyl-2-methoxy-3-phenoxy-3-(2-methoxy-phenyl)-propylamine;
N-methyl-2-methoxy-3-(2-methoxy-phenoxy)-3-(2-methoxy-phenyl)-propylamine;
N-methyl-2-methoxy-3-(2-ethoxy-phenoxy)-3-(2-methoxy-phenyl)-propylamine;
N-methyl-2-methoxy-3-phenoxy-3-(4-ethoxy-phenyl)-propylamine;
N-methyl-2-methoxy-3-(2-methoxy-phenoxy)-(3-(4-ethoxy-phenyl)-propylamine;
N-methyl-2-methoxy-3-(4-methoxy-phenoxy)-3-(4-ethoxy-phenyl)-propylamine;
N-methyl-2-methoxy-3-(2-ethoxy-phenoxy)-3-(4-ethoxy-phenyl)-propylamine;
N-methyl-2-methoxy-3-(4-ethoxy-phenoxy)-3-(4-ethoxy-phenyl)-propylamine;
N-methyl-2-methoxy-3-(2-trifluoromethyl-phenoxy)-3-(4-ethoxy-phenyl)-propylamine;
N-methyl-2-methoxy-3-(4-trifluoromethyl-phenoxy)-3-(4-ethoxy-phenyl)-propylamine;
N-methyl-2-methoxy-3-phenoxy-3-(2-chloro-phenyl)-propylamine;
N-methyl-2-methoxy-3-(2-methoxy-phenoxy)-3-(2-chloro-phenyl)-propylamine;
N-methyl-2-methoxy-3-(2-ethoxy-phenoxy)-3-(2-chloro-phenyl)-propylamine;
N-methyl-2-methoxy-3-phenoxy-3-(3-chloro-phenyl)-propylamine;
N-methyl-2-methoxy-3-(2-methoxy-phenoxy)-3-(3-chloro-phenyl)-propylamine;
N-methyl-2-methoxy-3-(2-ethoxy-phenoxy)-3-(3-chloro-phenyl)-propylamine;
N-methyl-2-methoxy-3-phenoxy-3-(4-chloro-phenyl)-propylamine;
N-methyl-2-methoxy-3-(2-methoxy-phenoxy)-3-(4-chloro-phenyl)-propylamine;
N-methyl-2-methoxy-3-(2-ethoxy-phenoxy)-3-(4-chloro-phenyl)-propylamine;
N-methyl-2-methoxy-3-phenoxy-3-(4-trifluoromethyl-phenyl)-propylamine;
N-methyl-2-methoxy-3-(2-methoxy-phenoxy)-3-(4-trifluoromethyl-phenyl)-propylamine;
N-methyl-2-methoxy-3-(4-methoxy-phenoxy)-3-(4-trifluoromethyl-phenyl)-propylamine;
N-methyl-2-methoxy-3-(2-ethoxy-phenoxy)-3-(4-trifluoromethyl-phenyl)-propylamine;
N-methyl-2-methoxy-3-(4-ethoxy-phenoxy)-3-(4-trifluoromethyl-phenyl)-propylamine;
N-methyl-2-methoxy-3-phenoxy-3-(3,4-dichloro-phenyl)-propylamine;
N-methyl-2-methoxy-3-(2-methoxy-phenoxy)-3-(3,4-dichloro-phenyl)-propylamine;
N-methyl-2-methoxy-3-(2-ethoxy-phenoxy)-3-(3,4-dichloro-phenyl)-propylamine.

EXAMPLE 3

Under an atmosphere of nitrogen to 15.7 g of 2-hydroxy-3-(2-chloro-phenyl)-3-(2-methoxy-phenoxy)-propionitrile in 110 ml of anhydrous THF there was added at 15° C. 46.2 ml of a 1.35 M solution of diborane in tetrahydrofuran. Stirring was continued at room temperature for 16 hours. A small quantity of ethanol was added and the whole was evaporated to dryness. The residue was dissolved in ethyl ether, extracted with 3% HCl, made alkaline with 20% NaOH, re-extracted with ethyl ether. After washing with water, drying over $Na_2SO_4$, filtration and evaporation to dryness, there was obtained 12.45 g of 2-hydroxy-3-(2-methoxy-phenoxy)-3-(2-chlorophenyl)-propylamine. Yield 78%.

All the primary amines useful for the preparation of the N-methyl derivatives mentioned in the examples 1 and 2 were analogously prepared.

EXAMPLE 4

To a mixture of 31.07 g of $LiAlH_4$ in 1500 ml of anhydrous ethyl ether a solution of 156.6 g of 2-hydroxy-3-(2-methoxy-phenoxy)-3-phenyl-propionitrile in 1200 ml of anhydrous ethyl ether and 150 ml of anhydrous THF, was added dropwise without cooling. The whole was stirred for 16 hours at room temperature and then refluxed for 1 hour, cooled to 0° C. and decomposed with 31 ml of $H_2O$, 31 ml of 15% NaOH, 93 ml of $H_2O$. The insoluble matter was filtered and well washed with ethyl acetate under heating.

After evaporating the solvent the residue was dissolved in 600 ml of ethyl ether; the whole was extracted with 3% HCl, made alkaline with 20% NaOH and re-extracted with ether. After normal processing there was obtained 86.2 g of 2-hydroxy-3-(2-methoxy-phenoxy)-3-phenyl-propylamine, melting point 80°–110° C. (Yield 54.4%), as a mixture of diastereoisomers in a ratio of approximately 1:1. The mixture was separated by chromatography on silica gel (phase: $CHCl_3/CH_3OH/32\%$ $NH_4OH$—150/50/2) in this way obtaining two distinct diastereoisomers having, respectively, melting point of 126°–129° C. (diastereoisomer with $R_f<$) and of 105°–110° C. (diastereoisomer with $R_f>$).

All the primary amines useful for the preparation of the N-methyl derivatives mentioned in the Examples 1 and 2, except those containing chloro, were similarly prepared.

EXAMPLE 5

2.69 g of 2-hydroxy-3-phenyl-3-(2-methoxy-phenoxy)-propionitrile dissolved in 25 ml of anhydrous DMF and 7.1 g of methyl iodide were stirred at 0° C. Addition was made, in portions, of 2.18 g of 55% NaH. After the addition, the whole was stirred at 0°–5° C. for 1 and a half hours. Under an atmosphere of nitrogen the whole was then decomposed cautiously with water, diluted with plentiful water, extracted with ethyl acetate and washed with water. The organic phase was dried over $Na_2SO_4$ and evaporated to dryness, in this way obtaining 1.95 g of 2-methoxy-3-phenyl-3-(2-methoxy-phenoxy)-propionitrile as an oil. Yield=69%.

Analogously, all the 2-methoxy-propionitrile derivatives useful for the preparation of the 2-methoxy-propylamines listed in Example 2 and obtained according to the reduction of Example 3, were prepared.

EXAMPLE 6

150 g of α-(2-methoxy-phenoxy)-phenyl acetaldehyde dissolved in approximately 1800 ml of diglyme was stirred with 176.5 g of sodium metabisulphite in 500 ml of water and 200 ml of ethanol at 50° C. for 16 hours. The whole was cooled to room temperature and addition was made of 44.4 g of potassium cyanide in 200 ml of water. The whole was stirred at 90° C. (external temperature) for 5 hours, concentrated to approximately 800 ml and poured into water: extraction was performed with 4×750 ml of ethyl ether and the whole washed with water, dried over $Na_2SO_4$ and evaporated to dryness to obtain 156.5 g of 2-hydroxy-3-phenyl-3-(2-methoxy-phenoxy)-propionitrile as a viscous oil. Yield=94%.

Analogously, all the 2-hydroxy-propionitrile derivatives useful for the preparation of the 2-hydroxy-propylamines mentioned in Examples 3 and 4 were prepared.

EXAMPLE 7

171 g of the chloride of α-(2-methoxy-phenoxy)-phenylacetic acid was dissolved in 1000 ml of anhydrous diglyme under stirring. At a temperature of between −60° C. and −65° C. there was added dropwise over two and a half hours 173 g of tris-tertbutoxy lithium aluminium hydride dissolved in 800 ml of anhydrous diglyme. When the addition was complete, the temperature was maintained at −60° C. for 30 minutes. The temperature was then allowed to rise to −40° C. and the mixture was decomposed with 152 g of ammonium sulphate in 228 ml of water. The whole was diluted with 2000 ml of ethyl ether and Celite was added. The whole was filtered at approximately 0° C. and then the residue was washed thoroughly with ethyl ether. The ether was concentrated under vacuum at below 30° C., to obtain a solution of diglyme containing α-(2-methoxy-phenoxy)-phenyl acetaldehyde in quantitative yield: this solution was used as such, to obtain the propionitrile of the Example 6.

Analogously, all the aldehydes useful for the preparation of the propionitrile derivatives obtained according to Example 6 were prepared.

EXAMPLE 8

0.47 g of α-(3-methoxy-phenoxy)-phenylacetic acid was dissolved in 20 ml of anhydrous benzene. At room temperature there was added dropwise 1.9 ml of oxalyl chloride diluted with 7 ml of anhydrous benzene. The whole was refluxed for 5 hours, then evaporated to dryness taking up twice with anhydrous benzene and again concentrating to dryness. There was in this way obtained the chloride of α-(3-methoxy-phenoxy)-phenylacetic acid with a quantitative yield of (0.50 g), which was used as such for the reduction to aldehyde reported in Example 7.

Analogously, all the acid chlorides useful for the preparation of the aldehydes mentioned in Example 7 were prepared.

EXAMPLE 9

160 g of α-(2-methoxy-phenoxy)-phenylacetic acid was mixed with 500 ml of thionyl chloride at room temperature. After 20 hours the reaction was complete. The whole was evaporated to dryness, taking up the residue twice with anhydrous benzene and again evaporating to dryness. There was in this way obtained with quantitative yield (171 g) the chloride of α-(2-methoxy-phenoxy)-phenylacetic acid which was used as such for the reduction to aldehyde reported in Example 7.

Analogously, the acid chlorides useful for the preparation of the aldehydes mentioned in Example 7 were prepared. The phenylacetic acids used as starting material for the preparation of the acid chlorides indicated in this example and Example 8 were known compounds which can be prepared with known methods, as for example described in *Bull. Soc. Chem. Fr.* 1956, 776.

EXAMPLE 10

50.3 g of N-methyl-2-hydroxy-3-phenyl-3-(2-nitrophenoxy)-propionamide dissolved in 1000 ml of anhydrous THF was reduced to amine by slowly adding at 8° C. 340 ml of a molar solution of diborane in THF. The whole was refluxed for 4 hours, cooled to room temperature, the excess of diborane was decomposed with MeOH and then, again at room temperature, dropwise addition was made of 400 ml of an ethereal solution of HCl. The whole was left to stand for 16 hours and then evaporated to dryness at reduced pressure, taken up with $CH_2Cl_2$ and washed once with an aqueous solution of sodium bicarbonate. The organic phase was then washed several times with a saturated aqueous solution of NaCl, dried with sodium sulphate and evaporated to dryness. The dark oil forming the residue was dissolved in 800 ml of ethyl ether and alcoholic hydrochloric acid (18% solution in ETOH) was added; there was obtained 50.9 g of N-methyl-2-hydroxy-3-(2-nitro-phenoxy)-3-phenyl-propylamine, hydrochloride, m.p. 197°–203° C. (yield 94%).

IR $\nu$max (KBr) 1525 cm$^{-1}$ ($NO_2$). 2700 cm$^{-1}$ ($NH_2^+$).

Analogously, all the compounds listed in Examples 1 and 2 were prepared.

EXAMPLE 11

40 g of ethyl-2-hydroxy-3-phenyl-3-(2-nitro-phenoxy)-propionate in 1 liter of 95° ethyl alcohol and 250 ml of 35% methylamine was heated in a stopped vessel at 40°–50° C. for 24 hours. The whole was evaporated to dryness under vacuum, taken up with 200 ml of absolute ethyl alcohol, again evaporated to dryness and the residue crystallized from isopropanol. There was in this way obtained 36 g (94.2%) of N-methyl-2-hydroxy-3-phenyl-3-(2-nitro-phenoxy)-propionamide, melting point 162°–163° C.

I.R. $\nu$max (nujol) 1640 cm$^{-1}$ (CON). 3300 cm$^{-1}$ (OH—broad band). 3400 cm$^{-1}$ (narrow, intense band).

Analogously, the propionamides useful for the preparation of the propylamines obtained according to Example 10 were prepared.

EXAMPLE 12

66 g of trans ethyl glycidate and 48 g of o-nitrophenol were dissolved in 1 liter of absolute ethyl alcohol to which 36 g of anhydrous $Na_2CO_3$ was added. The whole was refluxed under stirring for 48 hours, a further 24 g of o-nitrophenol was added and the whole was refluxed for another 36 hours, after which it was evaporated to dryness under vacuum, diluted with water and extracted with ethyl acetate which was then washed with 2 N NaOH until the excess phenol was wholly extracted. The whole was then washed with water to neutrality, dried over Na₂SO₄ and evaporated to dryness. The residue was crystallized from Et₂O to obtain 67 g (60%) of ethyl 2-hydroxy-3-phenyl-3-(2-nitrophenoxy)-propionate, m.p. 129°-131° C.

I.R. νmax (nujol) 1525 cm⁻¹ (NO₂). 3300 cm⁻¹ (OH broad band). 1740 cm⁻¹

Analogously, all the 2-hydroxy-propionates useful for the synthesis of the 2-hydroxy-propionamides obtained according to Example 11 (including the diastereoisomers obtained starting from the cis glicidates) were prepared.

EXAMPLE 13

To 2 g of ethyl 2-hydroxy-3-phenyl-3-(2-nitrophenoxy)-propionate dissolved in 30 ml of anhydrous dimethylformamide, CH₃I (0.78 ml) was added at 3° C., then, in two additions, at the same temperature, NaH 50% (0.3 g) was added too. The whole was stirred at 3° C. for one hour and at room temperature for one hour, after which it was poured into 300 ml of water, extracted with ethyl ether which, after washing with NaCl saturated water and dehydration with sodium sulphate, was evaporated to dryness under reduced pressure. There was obtained 2 g (96%) of ethyl 2-methoxy-3-phenyl-3-(2-nitro-phenoxy)-propionate as an oil.

I.R. νmax (film) 1740 cm⁻¹

1525 cm⁻¹ (NO₂).

N.M.R.: ppm (CDCl₃): 3.24 (3H).

Analogously, all the 2-methoxy-propionates useful for the preparation of the 2-methoxy-propionamides obtained according to Example 11 were prepared.

EXAMPLE 14

6.9 g of ethyl 3-phenyl-3-(2-nitro-phenoxy)-2-methoxy-propionate, dissolved in 150 ml of absolute ethanol, was hydrogenated (5% Palladium-charcoal) at ambient pressure and temperature.

The reaction was complete within 30 minutes. The catalyst was filtered and the solvent eliminated at reduced pressure. To the remaining oil, taken up with a small quantity of ethanol, there was added 4 ml of 18% HCl in ethanol. By diluting with ethyl ether there was obtained ethyl 3-(2-aminophenoxy)-3-phenyl-2-methoxy-propionate hydrochloride.

I.R. νmax (KBr) 2850 cm⁻¹ (ArNH₃⁺). 1740 cm⁻¹

N.M.R.: ppm (DMSO-d₆) 3.24 (s, 3H); 4.05 (q, 2H); 1.21 (t, 3H).

EXAMPLE 15

To a solution of 8 g of ethyl 3-(2-amino-phenoxy)-3-phenyl-2-methoxy-propionate, dissolved in 23% HCl (11.6 ml) at 4°-5° C., water (30 ml) was added and, always under cooling, a solution of NaNO₂ (1.73 g) dissolved in water (30 ml) was slowly dropped. The solution was stirred at room temperature for 30 minutes and then heated at 50° C. for 15 minutes; evolution of N₂ was noted. After extraction with CH₂Cl₂ and appropriate washings, the CH₂Cl₂ was evaporated to dryness so obtaining an oil, which was separated by column chromatography to give 4.0 g of ethyl 3-(2-hydroxyphenoxy)-3-phenyl-2-methoxy-propionate (50%).

I.R. νmax (CHCl₃) 3500 cm⁻¹ (OH dimer—broad band). 1740 cm⁻¹

EXAMPLE 16

To a solution of 9.5 g of ethyl-3-(2-hydroxy-phenoxy)-3-phenyl-2-methoxy-propionate in 130 ml of anhydrous dimethylformamide there was added 4.8 ml of anhydrous potassium carbonate and then, under stirring, dropwise addition was made of 2.2 ml of CH₃I in 15 ml of dimethylformamide. After four and a half hours the mixture was poured into 1 liter of water, then extracted twice with ethyl acetate. The extracts were combined, washed with water and dehydrated and then concentrated at reduced pressure. Chromatography on silica gel was performed to obtain 8.6 g of ethyl 3-phenyl-3-(2-methoxy-phenoxy)-2-methoxy propionate. Yield = 86.8%.

I.R. νmax (film) 2815 cm⁻¹ (OCH₃). 1738 cm⁻¹

EXAMPLE 17

To a solution of 2-[α-(2-methoxy-phenoxy)-4-chloro-benzyl]-morpholine (11.6 g) and triethylamine (3.5 g) in benzene (100 ml) a solution of CH₃I (5.5 g) in benzene (20 ml) was added dropwise at room temperature over 1 hour. Stirring was continued at room temperature for 20 hours, the mixture was filtered and the solvent was evaporated to dryness so obtaining an oil which was separated on silica gel column to give 4-methyl-2-[α-(2-methoxy-phenoxy)-4-chloro-benzyl]-morpholine (7 g; yield 57%).

Analgously, the following 4-methyl-morpholine derivatives were prepared:
4-methyl-2-(α-phenoxy-benzyl)-morpholine;
4-methyl-2-[α-(2-methoxy-phenoxy)-benzyl]-morpholine. HCl m.p. 67°-90° C.;
4-methyl-2-[α-(3-methoxy-phenoxy)-benzyl]-morpholine;
4-methyl-2-[α-(4-methoxy-phenoxy)-benzyl]-morpholine;
4-methyl-2-[α-(2-ethoxy-phenoxy)-benzyl]-morpholine;
4-methyl-2-[α-(4-ethoxy-phenoxy)-benzyl]-morpholine;
4-methyl-2-[α-(2-chloro-phenoxy)-benzyl]-morpholine;
4-methyl-2-[α-(4-chloro-phenoxy)-benzyl]-morpholine;
4-methyl-2-[α-(4-trifluoromethyl-phenoxy)-benzyl]-morpholine;
4-methyl-2-[α-(3,4-methylendioxy-phenoxy)-benzyl]-morpholine;
4-methyl-2-(α-phenoxy-2-methoxy-benzyl)-morpholine;

4-methyl-2-[α-(2-methoxy-phenoxy)-2-methoxy-benzyl]-morpholine;
4-methyl-2-[α-(2-ethoxy-phenoxy)-2-methoxy-benzyl]-morpholine;
4-methyl-2-(α-phenoxy-4-ethoxy-benzyl)-morpholine;
4-methyl-2-[α-(2-ethoxy-phenoxy)-4-ethoxy-benzyl]-morpholine;
4-methyl-2-[α-(4-ethoxy-phenoxy)-4-ethoxy-benzyl]-morpholine;
4-methyl-2-[α-(4-trifluoromethyl-phenoxy)-4-ethoxy-benzyl]-morpholine;
4-methyl-2-[α-(4-chloro-phenoxy)-4-ethoxy-benzyl]-morpholine;
4-methyl-2-[α-(2-methoxy-phenoxy)-4-ethoxy-benzyl]-morpholine;
4-methyl-2-[α-(4-methoxy-phenoxy)-4-ethoxy-benzyl]-morpholine;
4-methyl-2-(α-phenoxy-2-chloro-benzyl)-morpholine;
4-methyl-2-[α-(2-methoxy-phenoxy)-2-chloro-benzyl]-morpholine;
4-methyl-2-[α-(2-ethoxy-phenoxy)-2-chloro-benzyl]-morpholine;
4-methyl-2-(α-phenoxy-3-chloro-benzyl)-morpholine;
4-methyl-2-[α-(2-methoxy-phenoxy)-3-chloro-benzyl]-morpholine;
4-methyl-2-[α-(2-ethoxy-phenoxy)-3chloro-benzyl]-morpholine;
4-methyl-2-(α-phenoxy-4-chloro-benzyl)-morpholine;
4-methyl-2-[α-(2-ethoxy-phenoxy)-4-chloro-benzyl]-morpholine;
4-methyl-2-[α-(4-ethoxy-phenoxy)-4-chloro-benzyl]-morpholine;
4-methyl-2-[α-(4-methoxy-phenoxy)-4-chloro-benzyl]-morpholine;
4-methyl-2-[α-(4-chloro-phenoxy)-4-chloro-benzyl]-morpholine;
4-methyl-2-(α-phenoxy-4-trifluoromethyl-benzyl)-morpholine;
4-methyl-2-[α-(2-methoxy-phenoxy)-4-trifluoromethyl-benzyl]-morpholine;
4-methyl-2-[α-(4-methoxy-phenoxy)-4-trifluoromethyl-benzyl]-morpholine;
4-methyl-2-[α-(2-ethoxy-phenoxy)-4-trifluoromethyl-benzyl]-morpholine;
4-methyl-2-[α-(4-ethoxy-phenoxy)-4-trifluoromethyl-benzyl]-morpholine;
4-methyl-2-[α-(4-chloro-phenoxy)-4-trifluoromethyl-benzyl]-morpholine;
4-methyl-2-(α-phenoxy-3,4-dichloro-benzyl)-morpholine;
4-methyl-2-[α-(2-methoxy-phenoxy)-3,4-dichloro-benzyl]-morpholine;
4-methyl-2-[α-(2-ethoxy-phenoxy)-3,4-dichloro-benzyl]-morpholine.

EXAMPLE 18

To a solution of 2-[α-(2-methoxy-phenoxy)-4-chloro-benzyl]-morpholine (7.35 g) in CHCl$_3$ (50 ml), 2 N NaOH (18.2 ml) was added; the mixture was cooled to 0° C. and ethyl chloroformiate (3.5 ml) was dropped over 30 minutes. Stirring and cooling at 0° C. was maintained for 1 hour; the organic phase was separated, washed with water and dried over anhydrous CaCl$_2$. The evaporation to dryness of the solvent gave a colourless oil which was dissolved in diethyl ether (100 ml) and added, at room temperature, to a suspension of LiAlH$_4$ (2.5 g) in anhydrous diethyl ether (200 ml). The mixture was stirred at room temperature for 20 hours; water (2.5 ml), 15% NaOH (2.5 ml) and water (7.5 ml) were added. After filtration, the ethereal layer was separated and the aqueous phase was extracted with diethyl ether. The combined organic phases were washed with water and dried over anhydrous Na$_2$SO$_4$. After evaporation to dryness of the solvent, 4-methyl-2-[α-(2-methoxy-phenoxy)-4-chloro-benzyl]-morpholine was obtained as oil (6.25 g; yield 82%).

Analogously, all the 4-methyl-morpholine derivatives of the example 17 were prepared.

EXAMPLE 19

To a well stirred mixture of 2-[α-(2-methoxy-phenoxy)-2-chloro-benzyl]-morpholine (2 g) in glacial acetic acid (5.2 ml), acetone (12 ml) and water (8 ml), NaBH$_4$ (6.024 g) was added over 1 hour maintaining the temperature near 0° C. Then more acetone (12 ml) and NaBH$_4$ (3 g) were added; the temperature was allowed to rise to room temperature and after 30 hours the reaction mixture was poured into a solution of NaHCO$_3$ in water, then extracted with diethyl ether. The ethereal extracts were washed with water, dried over Na$_2$SO$_4$ and evaporated to dryness to give 4-isopropyl-2-[α-(2-methoxy-phenoxy)-2-chloro-benzyl]-morpholine (1.85 g; yield 82.3%) .HCl m.p. 200°–240° C.

Analogously, the following 4-isopropyl-morpholine derivatives were prepared:
4-isopropyl-2-(α-phenoxy-benzyl)-morpholine;
4-isopropyl-2-[α-(2-methoxy-phenoxy)-benzyl]-morpholine.HCl m.p. 196°–203° C;
4-isopropyl-2-[α-(3-methoxy-phenoxy)-benzyl]-morpholine;
4-isopropyl-2-[α-(4-methoxy-phenoxy)-benzyl]-morpholine;
4-isopropyl-2-[α-(2-ethoxy-phenoxy)-benzyl]-morpholine;
4-isopropyl-2-[α-(4-ethoxy-phenoxy)-benzyl]-morpholine;
4-isopropyl-2-[α-(2-chloro-phenoxy)-benzyl]-morpholine;
4-isopropyl-2-[α-(4-chloro-phenoxy)-benzyl]-morpholine;
4-isopropyl-2-[α-(4-trifluoromethyl-phenoxy)-benzyl]-morpholine;
4-isopropyl-2-[α-(3,4-methylendioxy-phenoxy)-benzyl]-morpholine;
4-isopropyl-2-(α-phenoxy-2-methoxy-benzyl)-morpholine;
4-isopropyl-2-[α-(2-methoxy-phenoxy)-2-methoxy-benzyl]-morpholine;
4-isopropyl-2-[α-(2-ethoxy-phenoxy)-2-methoxy-benzyl]-morpholine;
4-isopropyl-2-(α-phenoxy-4-ethoxy-benzyl)-morpholine;
4-isopropyl-2-[α-(2-ethoxy-phenoxy)-4-ethoxy-benzyl]-morpholine;
4-isopropyl-2-[α-(4-ethoxy-phenoxy)-4-ethoxy-benzyl]-morpholine;
4-isopropyl-2-[α-(4-trifluoromethyl-phenoxy)-4-ethoxy-benzyl]-morpholine;
4-isopropyl-2-[α-(4-chloro-phenoxy)-4-ethoxy-benzyl]-morpholine;
4-isopropyl-2-[α-(2-methoxy-phenoxy)-4-ethoxy-benzyl]-morpholine;
4-isopropyl-2-[α-(4-methoxy-phenoxy)-4-ethoxy-benzyl]-morpholine;
4-isopropyl-2-(α-phenoxy-2-chloro-benzyl)-morpholine;

4-isopropyl-2-[α-(2-ethoxy-phenoxy)-2-chloro-benzyl]-morpholine;
4-isopropyl-2-(α-phenoxy-3-chloro-benzyl)-morpholine;
4-isopropyl-2-[α-(2-methoxy-phenoxy)-3-chloro-benzyl]-morpholine;
4-isopropyl-2-[α-(2-ethoxy-phenoxy)-3-chloro-benzyl]-morpholine;
4-isopropyl-2-(α-phenoxy-4-chloro-benzyl)-morpholine;
4-isopropyl-2-[α-(2-ethoxy-phenoxy)-4-chloro-benzyl]-morpholine;
4-isopropyl-2-[α-(4-ethoxy-phenoxy)-4-chloro-benzyl]-morpholine;
4-isopropyl-2-[α-(2-methoxy-phenoxy)-4-chloro-benzyl]-morpholine;
4-isopropyl-2-[α-(4-methoxy-phenoxy)-4-chloro-benzyl]-morpholine;
4-isopropyl-2-[α-(4-chloro-phenoxy)-4-chloro-benzyl]-morpholine;
4-isopropyl-2-(α-phenoxy-4-trifluoromethyl-benzyl)-morpholine;
4-isopropyl-2-[α-(2-methoxy-phenoxy)-4-trifluoromethyl-benzyl]-morpholine;
4-isopropyl-2-[α-(4-methoxy-phenoxy)-4-trifluoromethyl-benzyl]-morpholine;
4-isopropyl-2-[α-(2-ethoxy-phenoxy)-4-trifluoromethyl-benzyl]-morpholine;
4-isopropyl-2-[α-(4-ethoxy-phenoxy)-4-trifluoromethyl-benzyl]-morpholine;
4-isopropyl-2-[α-(4-chloro-phenoxy)-4-trifluoromethyl-benzyl]-morpholine;
4-isopropyl-2-(α-phenoxy-3,4-dichloro-benzyl)-morpholine;
4-isopropyl-2-[α-(2-methoxy-phenoxy)-3,4-dichloro-benzyl]-morpholine;
4-isopropyl-2-[α-(2-ethoxy-phenoxy)-3,4-dichloro-benzyl]-morpholine.

EXAMPLE 20

To 33 g of 2-[α-(2-nitro-phenoxy)-benzyl]-morpholin-3-one dissolved in 60 ml of anhydrous THF there was added dropwise under stirring 16.7 ml of a 0.9 M solution of $BH_3$ in THF. The whole was heated at reflux for 3 hours and dropwise addition under cold conditions (0°–5° C.) was then made of 3 ml of methanol and then of 3 ml of 23% HCl. The solvent was removed under reduced pressure. The residue was diluted with $H_2O$, made alkaline and extracted with chloroform. The organic extracts were washed to neutrality, dried and evaporated to dryness, to obtain 2 8.6 g of 2-[α-(2-nitro-phenoxy)-benzyl]-morpholine. Yield 94%.

I.R. ν max ($CHCl_3$) 3320 $cm^{-1}$ (N-H). 1525 $cm^{-1}$ ($NO_2$).

Analogously, the following compounds were prepared:
2-(α-phenoxy-benzyl)-morpholine.HCl m.p. 199°–202° C.;
2-[α-(2-methoxy-phenoxy)-benzyl]morpholine.HCl m.p. 14020–170° C.;
2-[α-(3-methoxy-phenoxy)-benzyl]-morpholine, $n_D$ 1.5762.
2[α-(4-methoxy-phenoxy)-benzyl]-morpholine;
2[α-(2-ethoxy-phenoxy)-benzyl]-morpholine, one diastereoisomer m.p. 170°–1° C;
2-[α-(4-ethoxy-phenoxy)-benzyl]-morpholine;
2-[α-(2-chloro-phenoxy)-benzyl]-morpholine;
2-[α-(4-chloro-phenoxy)-benzyl]-morpholine;
2-[α-(4-trifluoromethyl-phenoxy)-benzyl]-morpholine;
2-[α-(3,4-methilendioxy-phenoxy)-benzyl]-morpholine.-HCl m.p. 82°–130° C.;
2-(α-phenoxy-2-methoxy-benzyl)-morpholine;
2-[α-(2-methoxy-phenoxy)-2-methoxy-benzyl]-morpholine, $n_D$ 1.5672;
2-[α-(2-ethoxy-phenoxy)-2-methoxy-benzyl]-morpholine;
2-(α-phenoxy-4-ethoxy-benzyl)-morpholine;
2-[α-(2-ethoxy-phenoxy)-4-ethoxy-benzyl]-morpholine;
2-[α-(4-ethoxy-phenoxy)-4-ethoxy-benzyl]-morpholine;
2-[α-(4-trifluoromethyl-phenoxy)-4-ethoxy-benzyl]-morpholine;
2-[α-(4-chloro-phenoxy)-4-ethoxy-benzyl]-morpholine;
2-[α-(2-methoxy-phenoxy)-4-ethoxy-benzyl]-morpholine;
2-[α-(4-methoxy-phenoxy)-4-ethoxy-benzyl]-morpholine;
2-(α-phenoxy-2-chloro-benzyl)-morpholine;
2-[α-(2-methoxy-phenoxy)-2-chloro-benzyl]-morpholine, m.p. 80°–102° C.;
2-[α-(2-ethoxy-phenoxy)-2-chloro-benzyl]-morpholine;
2-(α-phenoxy-3-chloro-benzyl)-morpholine;
2-[α-(2-methoxy-phenoxy)-3-chloro-benzyl]-morpholine;
2-[α-(2-ethoxy-phenoxy)-3-chloro-benzyl]-morpholine;
2-(α-phenoxy-4-chloro-benzyl)-morpholine;
2-[α-(2-ethoxy-phenoxy)-4-chloro-benzyl]-morpholine;
2-[α-(4-ethoxy-phenoxy)-4-chloro-benzyl]-morpholine;
2-[α-(2-methoxy-phenoxy)-4-chloro-benzyl]-morpholine;
2-[α-(4-metoxy-phenoxy)-4-chloro-benzyl]-morpholine;
2-[α-(4-chloro-phenoxy)-4-chloro-benzyl]-morpholine;
2-(α-phenoxy-4-trifluoromethyl-benzyl)-morpholine;
2-[α-(2-methoxy-phenoxy)-4-trifluoromethyl-benzyl]-morpholine;
2-[α-(4-methoxy-phenoxy)-4-trifluoromethyl-benzyl]-morpholine;
2-[α-(2-ethoxy-phenoxy)-4-trifluoromethyl-benzyl]-morpholine;
2-[α-(4-ethoxy-phenoxy)-4-trifluoromethyl-benzyl]-morpholine;
2-[α-(4-chloro-phenoxy)-4-trifluoromethyl-benzyl]-morpholine;
2-(α-phenoxy-3,4-dichloro-benzyl)-morpholine;
2-[α-(2-methoxy-phenoxy)-3,4-dichloro-benzyl]-morpholine;
2-[α-(2-ethoxy-phenoxy)-3,4-dichloro-benzyl]-morpholine;
as well as all the compounds mentioned in Examples 17 and 19.

EXAMPLE 21

To a solution of 4.24 g of N-(2-mesyloxyethyl)-3-phenyl-2-hydroxy-3-(2-nitro-phenoxy)-propionamide in 150 ml of DMF there was added 1.38 g of potassium carbonate. The stirred mixture was heated at 50° C. for 5 hours, then poured into water and extracted with ethyl acetate. The dehydrated organic extracts were evaporated to dryness and the residue was chromatographed on silica gel, to obtain 1.27 g of 2-[α-(2-nitro-phenoxy)-benzyl]-morpholin-3-one. Yield 38.6%.

I.R. ν max (nujol) 3450 $cm^{-1}$ (NH). 1670 $cm^{-1}$ (CONH). 1525 $cm^{-1}$ ($NO_2$).

Analogously, the morpholin-3-one derivatives useful for the preparation of the compounds mentioned in the Examples 17, 19 and 20 were prepared.

EXAMPLE 22

To 5.2 g of N-(2-hydroxy-ethyl)-3-phenyl-2-hydroxy-3-(2-nitrophenoxy)-propionamide dissolved in 200 ml of anhydrous THF there was added 2.4 ml of triethylamine. The solution was cooled to −10° C. and, under stirring, slow dropwise addition was made of a solution of 1.83 f of mesyl chloride in 30 ml of THF. After 45 minutes at −10° C. the temperature was allowed to rise to room temperature. The solution was concentrated to a small volume at reduced pressure. The residue was poured into water. The mixture was extracted with chloroform, the extracts washed to neutrality with water and then dried over sodium sulphate.

The solvent was removed at reduced pressure and the residue was crystallized from 95° ethanol, to obtain 4.86 g of N-(2-mesyloxy-ethyl)-3-phenyl-2-hydroxy-3-(2-nitrohenoxy)-propionamide, m.p. 122°–125° C. (yield 76.5%).

I.R. $\nu$ max (KBr) 3500 cm$^{-1}$ (OH— broad band). 3450 cm$^{-1}$ (NH). 1650 cm$^{-1}$ (CONH). 1525 cm$^{-1}$ (NO$_2$). 1350 cm$^{-1}$ (SO$_2$). 1180 cm$^{-1}$ (SO$_2$).

Analogously, the N-(2-mesyloxy-ethyl)-propionamides useful for the preparation of the compounds mentioned in Example 21 were prepared.

EXAMPLE 23

3 g of ethyl-3-phenyl-2-hydroxy-3-(2-nitrophenoxy)-propionate was refluxed with 5.4 ml of ethanolamine in 50 ml of anhydrous ethanol for 20 hours. The solvent was removed under reduced pressure, the residue was taken up with water and the solid collected by filtration. After crystallization from ethyl acetate, 1.8 g of N-(2-hydroxyethyl)-3-phenyl-2-hydroxy-3-(2-nitrophenoxy)-propionamide was obtained, m.p. 166°–188° C. Yield 58%.

I.R. $\nu$ max (nujol) 3400 cm$^{-1}$ (OH, NH— broad band). 1650 cm$^{-1}$ (CONH). 1525 cm$^{-1}$ (NO$_2$).

Analogously, the N-(2-hydroxy-ethyl)-propionamides useful for the preparation of the compounds mentioned in Example 22 were prepared.

EXAMPLE 24

A mixture of 0.9 g of 2-($\alpha$-phenoxy-carbonyloxy-benzyl)-morpholin-3-one in 2.5 ml of HMPT was heated to 140° C. After 1 hour the reaction was complete. The whole was diluted with water and extracted with ethyl acetate. The organic extracts were washed with water, dried over Na$_2$SO$_4$, filtered and concentrated to dryness, to obtain 2-($\alpha$-phenoxy-benzyl)-morpholin-3-one. There were similarly prepared all the morpholin-2-one derivatives necessary for the preparation of the Example 20.

EXAMPLE 25

To 0.6 g 2-($\alpha$-hydroxy-benzyl)-morpholin-3-one dissolved in 5 ml of anhydrous pyridine at 0° C. there was added dropwise 0.5 g of phenyl chloroformate. The whole was stirred at room temperature for 12 hours. Addition was made of 30 ml of CH$_2$Cl$_2$, washing was performed with 5% HCl then with 5% NaOH and finally with water. The organic phase was dried over Na$_2$SO$_4$. The whole was filtered and evaporated to dryness to obtain 2-($\alpha$-phenoxy-carbonyloxy-benzyl)-morpholin-3-one. Yield 95% Similarly, all the analogous intermediates useful as starting materials for the preparation of the compounds of Example 24 were prepared.

EXAMPLE 26

Under an atmosphere of nitrogen and in a anhydrous apparatus a mixture of 2.02 g of morpholin-3-one in 60 ml of anhydrous THF was stirred. Dropwise addition was made at room temperature of 26.7 ml of 15% butyl lithium in hexane over 45 minutes. After 2.5 hours of stirring at room temperature the whole was cooled to −62° C. and a solution of 2.02 ml of freshly distilled benzaldehyde in 10 ml of anhydrous THF was added, over 45 minutes. The mixture was kept at −62° C. for 3 hours, allowed to rise to room temperature and kept at this temperature for a further 16 hours. A little water was added and the whole was evaporated to dryness. The residue was taken up with a dilute solution of NaHCO$_3$, extracted with ethyl acetate and washed with H$_2$O. The solution was dried over Na$_2$SO$_4$, filtered and evaporated to dryness. The solid residue was ground with 40 ml of ethyl ether and filtered, to obtain 2.4 g of 2-($\alpha$-hydroxy-benzyl)-morpholin-3-one which was crystallized from ethyl acetate, melting point 130°–140° C. Yield 58.0%.

I.R. $\nu$ max (CHCl$_3$) 3400 cm$^{-1}$ (OH— broad band). 3300–3200 cm$^{-1}$ (NH). 1660 cm$^{-1}$ (CO).

Analogously, all the intermediates useful as starting materials for the preparation of the compounds of Example 25 were prepared.

EXAMPLE 27

To a suspension of 0.55 g of LiAlH$_4$ in 18 ml of anhydrous tetrahydrofuran there was added dropwise at 30° C. over 4 hours 1 g of 2-hydroxy-1-nitro-3-phenyl-3-(2-methoxy-phenoxy)-propane sodium salt in 70 ml of anhydrous tetrahydrofuran. After the addition, the mixture was cooled and decomposed with water, 15% NaOH, water. It was then filtered; the solid was washed with tetrahydrofuran and the solvent evaporated to dryness. The residue was dissolved in ethyl ether and extracted with 3% HCl, made alkaline with 20% NaOH NaOH and re-extracted with ethyl ether. The organic solution was then washed with water, dried over Na$_2$SO$_4$, filtered and evaporated to dryness. A small quantity of isopropyl ether was then used to ground it to obtain 2-hydroxy-3-(2-methoxy-phenoxy)-3-phenyl-propylamine (0.4 g); melting point 84°–110° C. (R=47.2%) as mixture of two diastereoisomers. The mixture was separated by column chromatography on silica gel (phase: CHCl$_3$/CH$_3$OH/32% NH$_4$OH-150/50/2) to obtain two distinct diastereoisomers having melting point of 126°–129° C. (diastereoisomer with Rf<) and 105°–110° C. respectively (diastereoisomer with Rf>).

Analogously, all the primary amines useful for the preparation of the N-methyl-derivatives mentioned in Examples 1 and 2 were prepared.

EXAMPLE 28

(a) To a suspension of 6 g of (2-methoxh-phenoxy)-phenylacetic acid in 50 ml of anhydrous tetrahydrofuran there was added 4.52 g of carbonyldiimidazole in 65 ml of anhydrous tetrahydrofuran. The whole was heated at reflux for one hour. This solution was used as such in (b).

(b) Under an atmosphere of nitrogen there was washed three times 1.21 g of 55% sodium hydride with anhydrous pentane; the whole was covered with 40 ml of anhydrous tetrahydrofuran and dropwise addition was made under stirring of 5.7 ml of nitromethane.

After fifteen minutes the solution (a) was added to this suspension over 10 minutes. The whole was heated at reflux for 16 hours, cooled and filtered. The solid, which was the starting product, was washed with 2×100 ml of $CH_2Cl_2$. The solution of tetrahydrofuran was combined with the $CH_2Cl_2$ and evaporated to dryness, taken up with hot 99° ethanol, cooled to room temperature and filtered.

There was obtained 4.1 g of 2-hydroxy-1-nitro-3-phenyl-3-(2-methoxy-phenoxy)-propene sodium salt, m.p. 120°–135° C. (yield 82%).

I.R. $\nu$ max (KBr) 2840 cm$^{-1}$ (Ar—O—$CH_3$). 1460–1350 cm$^{-1}$ (C=C—$NO_2$).

N.M.R.: ppm (CDCl$_3$); 7.05 (m, 5H); 6.8 (s, H); 6.6 (m 4H); 5.1 (s, H); 3.45 (s, 3H).

Analogously, all the nitro-derivatives useful for the synthesis of the 2-hydroxy-propylamines obtained according to Example 27 were prepared.

EXAMPLE 29

A solution of 1 g of 2-hydroxy-3-phenyl-3-(2-methoxy-phenoxy-1-nitro-propane sodium salt in 5 ml of anhydrous DMA and 0.623 ml of $CH_3I$ was stirred at 40° C. for 6 hours. The whole was poured into water and extracted with ethyl acetate, then washed with water and dried over $Na_2SO_4$. After filtration and evaporated to dryness there was obtained 0.90 g of 3-phenyl-2-methoxy-3-(2-methoxy-phenoxy)-1-nitro-propene, Yield=92%.

The compounds obtained according to the Example 28 were methylated similarly.

EXAMPLE 30

25.6 g of 3-(2-methoxy-phenoxy)-3-phenyl-propylene-1,2-oxide was dissolved in 60 ml of benzylamine. The whole was heated at 120° C. for 8 hours, the excess of benzylamine was distilled and poured into water; the aqueous solution was extracted 4 times with $Et_2O$ for a total of 1000 ml, washing was effected with plentiful water, and the $Et_2O$ was evaporated to dryness to obtain 25.2 g (69.4%) of N-benzyl-2-hydroxy-3-(2-methoxy-phenoxy)-3-phenyl-propylamine, as a clear colourless oil.

All the primary and secondary 2-hydroxy-propylamines indicated in the Examples 1, 3 and 4 were similarly prepared.

EXAMPLE 31

To a solution of 2.4 g of 3-(2-methoxy-phenoxy)-3-phenyl-propylene dissolved in 20 ml of $CH_2Cl_2$, MCPBA (1.9 g) was added at room temperature and the whole was kept under stirring for approximately two hours. The m-chlorobenzoic acid was separated by filtration, the organic layer was washed with water and then with saturated solutions of $Na_2S_2O_5$, $NaHCO_3$ and then again with water. The organic phase was dried over $Na_2SO_4$ and evaporated to dryness to obtain 1.6 g (62.5%) of 3-(2-methoxy-phenoxy)-3-phenyl-propylene-1,2-oxide. Similarly, all the propylene-1,2-oxide-derivatives useful for the preparation of the 2-hydroxy-propylamines of the Example 30 were prepared.

EXAMPLE 32

To a solution of 5 g of guaiacol sodium salt in 60 ml of dimethylformamide, 1-phenylallyl-chloride (5.22 g) (J.C.S. 1959, p. 2720) was added under a nitrogen atmosphere. The whole was stirred for 4 hours at room temperature and for two hours at 50° C., poured into water and extracted with ethyl ether. After standard working up, followed by chromatographic separation, 3-(2-methoxy-phenoxy)-3-phenyl-propylene (8.1 g; 98%) was obtained.

Analogously, the propylene derivatives useful for the preparation of the compounds indicated in the Example 31 were prepared.

EXAMPLE 33

Into a solution of 12.3 g of 2-[α-(2-nitro-phenoxy)-benzyl]-4-methyl-morpholin-5-one in 350 ml of anhydrous THF there was slowly added dropwise 77 ml of a molar solution of $BH_3$ in THF. After the addition, the mixture was refluxed for 6 hours. The excess of $BH_3$ was eliminated with MeOH at room temperature, and dropwise addition was then made to the reaction mixture of 50 ml of 23% HCl and stirring carried out for 1 hour at 60° C. The whole was concentrated to a small volume and the residue diluted with water, thereafter alkalinizing with NaOH and extracting with $CH_2Cl_2$. After normal processing and crystallization from isopropyl ether, the 2-[α-(2-nitro-phenoxy)-benzyl]-3-methyl-morpholine, m.p. 78°–81° C. (8.1 g; 68%) was obtained.

I.R. $\nu$max (CHCl$_3$) 1525 cm$^{-1}$ ($NO_2$).

N.M.R. ppm (CDCl$_3$) 5.3 (d, H benzylic) 7.4–6.8 (s, 9H aromatic) 2.27 (s, $CH_3$).

Analogously, the morpholin-5-one derivatives obtained in the examples 36, 37, 38 and all the morpholin-5-one derivatives corresponding to the compounds of the examples 17, 19 and 20 were reduced to the corresponding morpholines.

EXAMPLE 34

To 24.7 g of N-chloroacetyl-N-methyl-2-hydroxy-3-phenyl-3-(2-nitrophenoxy)-propylamine dissolved in 300 ml of anhydrous DMF there was added 3.5 g of 50% NaH in mineral oil. The reaction mixture was heated at 50° C. for 3 hours under stirring and then allowed to stand for 16 hours, then poured into 2 liters of water: a brown solid was separated and was filtered and purified by mixing with boiling 95% ETOH. There was obtained 18 g (Yield 80%) of 2-[α-(2-nitro-phenoxy)-benzyl]-4-methyl-morpholin-5-one, m.p. 192°–195° C.

I.R. $\nu$max (nujol) 1660 cm$^{-1}$ (CON). 1525 cm$^{-1}$ ($NO_2$).

The morpholin-5-one derivatives corresponding to the compounds of the Examples 17, 19 and 20 were similarly prepared.

EXAMPLE 35

To 55 g of N-methyl-2-hydroxy-3-phenyl-3-(2-nitro-phenoxy)-propylamine hydrochloride dissolved in 770 ml of distilled water there was added at room temperature 185 ml of 2 N NaOH and 200 ml of $CH_2Cl_2$. At 0° C., slow dropwise addition was made to the mixture of 16.7 ml of chloroacetyl chloride dissolved in 350 ml of anhydrous $CH_2Cl_2$. The solution was stirred at room temperature for 3 hours. The organic phase was separated and washed with an aqueous solution of bicarbonate, then with a saturated solution of NaCl, then dried and evaporated to dryness. There was obtained 60 g (Yield 97%) of N-chloroacetyl-N-methyl-3-phenyl-2-hydroxy-3-(2-nitro-phenoxy)-propylamine.

I.R. $\nu$max (CHCl$_3$) 3500 cm$^{-1}$ (OH—broad band); 1640 cm$^{-1}$ (CON); 1525 cm$^{-1}$ ($NO_2$).

The analogous intermediates useful for the preparation of the morpholin-5-one derivatives of the Example 34 were similarly prepared.

EXAMPLE 36

To a solution of 7 g of 2-[α-(2-nitro-phenoxy)-benzyl]-4-methyl-morpholin-5-one in 200 ml of DMF, 5% Palladium-charcoal (0.7 g) was added and the mixture was hydrogenated at 3.5 atmospheres for 0.5 hours. The catalyst was filtered off, the solution was poured into water and then extracted with ethyl acetate. After anhydrification and evaporation to dryness of the solvent, crystallization from ethyl ether gave 2-[α-(2-aminophenoxy)-benzyl]-4-methyl-morpholin-5-one, m.p. 167°–170° C. (5.3 g; 75.2%).

I.R. $\nu$max (nujol) 3300 cm$^{-1}$ (NH$_2$); 1660 cm$^{-1}$ (CON).

EXAMPLE 37

10 g of 2-[α-(2-amino-phenoxy)-benzyl]-4-methyl-morpholin -5-one was dissolved at 0° C. in 32 ml of 35% H$_2$SO$_4$. At this temperature slow addition was made of 2.76 g of NaNO$_2$ dissolved in 40 ml of H$_2$O and the mixture was kept under stirring in cold conditions for 20 minutes. Still at 0° C. there was added 120 g of Cu(-NO$_3$)$_2$ dissolved in 1000 ml of H$_2$O and 4.2 g of Cu$_2$O. After 5 minutes extraction was performed in cold conditions with ethyl acetate; the organic phase was washed to neutrality with a saturated aqueous solution of NaCl, dehydrated with sodium sulphate and evaporated to dryness. There was obtained a yellow oil which was separated by column chromatography on silica gel (phase:ethyl acetate/cyclohexane 2:1). There was obtained 6 g (Yield 60%) of 2-[β-(2-hydroxy-phenoxy)-benzyl]-4-methyl-morpholin-5-one.

I.R. $\nu$max (CHCl$_3$) 3500 cm$^{-1}$ (OH); 1660 cm$^{-1}$ (CON).

EXAMPLE 38

To a solution of 10 g of 2-[α-(2-hydroxy-phenoxy)-benzyl]-4-methylmorpholin -5-one in 150 ml of anhydrous DMF addition was made of 4.8 g of potassium carbonate, and then dropwise addition was made under stirring of 2.6 ml of bromoethane in 20 ml of DMF. The mixture was heated for 4 hours at 60° C. under stirring. The mixture was poured into 1.5 liters of water and extracted with ethyl acetate. The organic extracts were washed with H$_2$O, dehydrated over Na$_2$SO$_4$ and concentrated under reduced pressure. There was obtained 8.49 g (Yield 78%) of 2-[α-(2-ethoxy-phenoxy)-benzyl]-4-methyl-morpholin -5-one.

I.R. $\nu$max (nujol) 1660 cm$^{-1}$ (CON).

EXAMPLE 39

A solution of 6.8 g of 2-[α-(2-methoxyphenoxy)-benzyl]-4-methylmorpholin-3,5-dione in 40 ml of anhydrous tetrahydrofuran was added dropwise under stirring to a suspension of lithium aluminium hydride (1.9 g) in 35 ml of THF. The mixture was refluxed under stirring for 6 hours. Dropwise addition was then made at 0°–5° C. of 4.1 ml of 23% HCl and the whole was stirred at room temperature for 2 hours. The suspended solid was filtered and washed several times with THF. The combined filtrates were evaporated to dryness under reduced pressure. The residue was taken up with ethyl ether and 4 ml of 18% methanolic HCl was added. The amorphous hydrochloride precipitated which was washed several times with fresh ethyl ether. By filtration there was obtained 5.8 g of 2-[α-(2-methoxyphenoxy)-benzyl]-4-methyl-morpholine hydrochloride, melting point 67°–90° C. Yield 84%.

I.R. $\nu$max (KBr) 2700 cm$^{-1}$ (NH+) 2815 cm$^{-1}$ (OCH$_3$).

All the compounds mentioned in the Examples 17, 19 and 20, except those containing chloro, were similarly prepared. The same reaction described in Example 39 was carried out with diborane using the procedure of Example 20; in this way all the compounds mentioned in the Examples 17, 19 and 20 were also prepared.

EXAMPLE 40

4 g of ethyl 2-ethoxycarbonylmethyloxy-3-phenyl-3-(2-methoxyphenoxy)propionate dissolved in 30 ml of ethanol was heated in an autoclave at 150° C. for 20 hours with 20 ml of a 10% ethanolic solution of methylamine. Cooling was allowed to take place and the solvent was removed under reduced pressure. The residue was crystallized from ethanol to obtain 2.26 g of 2-[α-(2-methoxyphenoxy)-benzyl]-4-methyl-morpholin-3,5-dione. Yield 64%.

I.R. $\nu$max (CHCl$_3$) 1680 cm$^{-1}$ (CONCO); 1625 cm$^{-1}$ (CONCO).

Analogously, the morpholin-3,5-dione derivatives useful as intermediates for the preparation of the compounds of Example 39 were prepared.

EXAMPLE 41

A solution of 3.85 g of ethyl 2-hydroxy-3-phenyl-3-(2-methoxyphenoxy) propionate in 35 ml of DMF was heated at 60° C. under stirring for 60 hours with 5.34 ml of ethyl bromoacetate and 3.32 g of anhydrous potassium carbonate. The mixture was then poured into water, extracted with ethyl acetate and the organic extracts were washed to neutrality with H$_2$O, dehydrated, concentrated under reduced pressure and the residue chromatographed on silica gel (phase:ethyl acetate/cyclohexane 1/1) so obtaining 3.35 g of ethyl 2-(ethoxycarbonyl-methyloxy)-3-phenyl-3-(2-methoxy-phenoxy)-propionate. Yield 67%.

I.R. $\nu$max (film) 1815 cm$^{-1}$ (OCH$_3$); 1740 cm$^{-1}$

Similarly, the analogous intermediates useful for the preparation of the compounds of Example 40 were prepared.

EXAMPLE 42

To 3.55 g of 2-ethoxycarbonyl-methyloxy-3-phenyl-3-(2-methoxyphenoxy)-propionitrile dissolved in 40 ml of anhydrous THF and cooled to 10° C. under an atmosphere of nitrogen, slow dropwise addition was made, under stirring, of 15 ml of a molar solution of diborane in tetrahydrofuran. The mixture was then stirred at room temperature for 16 hours, cooled and decomposed cautiously with 3% HCl. The THF was evaporated and the residue was purified by dissolving it in 3% HCl, alkalinizing with sodium bicarbonate and extracting with ethyl ether.

The whole was evaporated to dryness to obtain 2.8 g of an oil which was dissolved in 30 ml of anhydrous THF. The solution obtained was refluxed for 4 hours. After cooling to 10° C. there was added dropwise 11.7 ml of a molar solution of diborane in THF. The whole was stirred at room temperature for 16 hours. The reaction mixture was decomposed cautiously with 3% HCl; the THF was removed under vacuum at room temperature and the acid aqueous solution was washed once with ethyl ether, made alkaline with $NaHCO_3$ and re-extracted with ethyl ether. The organic phase was washed with $H_2O$, dried over $NaSO_4$ and the residue converted to the hydrochloride which was crystallized from isopropanol and a small quantity of ethyl ether. There was obtained 2.2 g of 2-[α-(2-methoxyphenoxy)-benzyl]-morpholinehydrochloride, melting point 140°–170° C. (Yield 84.3%) as a mixture of diastereoisomers in the approximate ratio of 1:1. The mixture was separated by column chromatography on silica gel (phase:$CHCL_3/CH_3OH/HCOOH$—160/30/20), thus obtaining two distinct diastereoisomers having melting point respectively of 211°–214° C. (diastereoisomer with Rf>) and 175°–178° C. (diastereoisomer with Rf<).

Analogously, all the morpholines unsubstituted in the 4-position mentioned in Example 20 were prepared.

EXAMPLE 43

2.69 g of 2-hydroxy-3-phenyl-3-(2-methoxy-phenoxy)-propionitrile in 25 ml of anhydrous DMA was stirred with 6.68 g of ethyl bromoacetate in the presence of 2.76 g of anhydrous potassium carbonate. The mixture was heated at 50° C. for 16 hours, poured into water and extracted with ethyl acetate. The organic phase was washed with water, dried over $Na_2SO_4$ and concentrated to dryness, to obtain 3.55 g of 2-ethoxycarbonylmethyloxy-3-phenyl-3-(2-methoxyphenoxy)-propionitrile (oil) (Yield 100%), which was used as such for the reaction described in the previous example.

Analogously, the 2-ethoxycarbonylmethyloxy-propionitriles useful as intermediates to the synthesis of the compounds of Example 42 were prepared.

EXAMPLE 44

To 3.87 g of 2-ethoxycarbonylmethyloxy-3-phenyl-3-(2-methoxyphenoxy)-1-nitro-propene in 40 ml of anhydrous THF, at approximately 30° C., there was very slowly added a solution of 1.7 g of $LiAlH_4$ in 35 ml of anhydrous THF, under stirring, over approximately 2 hours. After the addition, the mixture was refluxed for 2 hours, cooled and treated with water, then with 15% soda and then again with water. After filtration, the solid was washed with THF and the organic solvent was evaporated to dryness. A purification—HCl (3%), NaOH (20%)—was then made, using ethyl ether as solvent. The residual oil of the concentration was converted into the hydrochloride which was crystallized 3 times from isopropanol plus a small quantity of ethyl ether, to obtain 2-[α-(2-methoxyphenoxy)-benzyl]-morpholine-hydrochloride (1.6 g), melting point 140°–170° C. (Yield 47.8%), as a mixture of diastereoisomers in the approximate ratio of 1:1. By means of chromatography, proceeding as described in Example 42, there were obtained two distinct diastereoisomers with melting point of respectively 211°–214° C. and 175°–178° C.

Analogously, all the morpholines unsubstituted in the 4-position mentioned in Example 20, except the compounds containing chloro, were prepared.

EXAMPLE 45

To 3.23 g of 2-hydroxy-3-phenyl-3-(2-methoxyphenoxy)-1-nitropropene sodium salt dissolved in 50 ml of anhydrous THF there was added at 0° C. 16.7 g of ethyl bromoacetate. After 2 hours at 0° C. the mixture was stirred at room temperature for 48 hours. The mixture was poured into water and extracted with ethyl acetate. The organic extracts were washed with water, dried over $Na_2SO_4$ and concentrated to dryness. The residue was separated by column chromatography on silica gel (mobile phase:ethyl acetate/cyclohexane 1/1), to obtain 2.70 g of 2-ethoxycarbonylmethyloxy-3-phenyl-3-(2-methoxy-phenoxy)-1-nitropropene (oil). Yield 70%.

Analogously, all the nitro-propene derivatives useful as intermediates for the preparation of the compounds of Example 44 were prepared.

EXAMPLE 46

3.35 g of N-(2-chloro-ethyl)-2-hydroxy-3-phenyl-3-(2-methoxy-phenoxy)-propylamine was dissolved in 40 ml of anhydrous THF at −10° C. At this temperature, slow dropwise addition was made to the mixture of 6.07 ml of 15% butyl lithium in hexane. After approximately 2 hours at −10° C. the temperature was slowly allowed to return to room temperature and the whole was stirred for another 20 hours in these conditions, and then concentrated to dryness. The residue was dissolved in ethyl ether, filtered and the filtrate again concentrated to dryness. The residue was converted to the hydrochloride by treatment with gaseous HCl in ethyl ether. After three crystallizations from a mixture of isopropanol and a very small quantity of ethyl ether, there was obtained 1.2 g of 2-[α-(2-methoxy-phenoxy)-benzyl]-morpholine hydrochloride, melting point 112°–170° C. (Yield 35.7%) as a mixture of diastereoisomers. By means of chromatographic separation, as described in Examples 42 and 44, there were obtained two distinct diastereoisomers having melting point of 211°–214° C. and 175°–178° C. respectively.

Analogously, all the compounds mentioned in the Examples 17, 19 and 20 were prepared.

EXAMPLE 47

To a solution of N-chloro-acetyl-3-phenyl-2-hydroxy-3-(2-methoxy-phenoxy)-propylamine (3.49 g) in anhydrous THF (35 ml), a molar solution of diborane in tetrahydrofurane (15 ml) is slowly added dropwise at −5° C. under stirring. The mixture was again stirred in cold conditions for 2 hours and then for 16 hours at room temperature. The mixture was cautiously decomposed with a small quantity of 99° ethanol, concentrated to dryness at a temperature below 20° C., to obtain N-(2-chloroethyl)-3-phenyl-2-hydroxy-3-(2-methoxyphenoxy)-propylamine (3.35 g; 100%) (oil).

This was used immediately as such for the conversion described in the previous example.

Analogously, all the N-(2-chloroethyl)-propylamines useful as intermediates for the preparation of the compounds of Example 46 were prepared.

EXAMPLE 48

A mixture of 2.73 g of 3-phenyl-2-hydroxy-3-(2-methoxy-phenoxy)-propylamine in 50 ml of methylene chloride and 0.56 g of NaOH in 15 ml of water was stirred at 0° C. Under vigorous stirring dropwise addition was made to the mixture over 30 minutes, again at 0° C., of 1.58 g of chloroacetyl chloride in 2 ml of methylene chloride. After the addition, the stirring was continued at 0° C. for 30 minutes. The layers were separated and the aqueous phase extracted with $CH_2Cl_2$. The organic extracts were combined and washed with water, dried over Na$_2$SO$_4$ and evaporated to dryness. There was obtained 3.49 g of N-chloroacetyl-2-hydroxy-3-phenyl-3-(2-methoxy-phenoxy)propylamine (oil). Yield 100%.

Analogously, all the intermediates useful as starting materials for the preparation of the compounds of Example 47 were prepared.

EXAMPLE 49

0.82 g of 2-hydroxy-3-phenyl-3-phenoxy-propylamine was stirred at 0° C. with 0.654 g of ethylene glycol dimethanesulphonate in 20 ml of anhydrous benzene. These conditions were kept for 20 hours. Again at 0° C., under cooling and vigorous stirring, dropwise addition was then made to the suspension of 3.65 ml of 15% butyl lithium in hexane. The mixture was kept at 0° C. for 2 hours and then at room temperature for 20 hours. A few drops of water were cautiously added to the mixture, which was then evaporated to dryness. A small quantity of water was added to the residue and the whole was then extracted with ethyl acetate. The organic phase was washed with water, dried over Na$_2$SO$_4$ and evaporated to dryness. The residue dissolved in ethyl ether was changed into the hydrochloride by treatment with alcoholic HCl and, after two crystallizations from a mixture of isopropanol and a small quantity of ethyl ether, there was obtained 0.50 g of 2-($\alpha$-phenoxy-benzyl)morpholine hydrochloride, melting point 140°–170° C. Yield 49.4%. Analogously, all the compounds mentioned in Examples 17, 19 and 20 were prepared.

EXAMPLE 50

To a solution of 2-hydroxy-3-(2-methoxy-phenoxy)-3-phenyl-propylamine (10 g) in anhydrous dimethylformamide (150 ml), 55% NaH (1.75 g) was added at room temperature. After stirring for 1 hour, a solution of 2-chloro-1-iodo-ethane (7 g) in dimethylformamide (50 ml) was added all at one time. The temperature was maintained at 50° C. for 1 hour then Na$_2$CO$_3$ (5.82 g) was added and the whole was maintained at 50° C. for a further 3 hours. The whole was poured into water and extraction made with ethyl acetate. After a standard working up, procedure, 2-[$\alpha$-(2-methoxy-phenoxy)-benzyl]-morpholine (6.24 g; 57%) was obtained as a transparent oil. HCl m.p. 140°–170° C. All the compounds mentioned in the Examples 17, 19 and 20 were similarly prepared.

EXAMPLE 51

To 3 g of 2-[$\alpha$-(2-aminophenoxy)-benzyl]-4-methyl morpholine dissolved in 30 ml of acetonitrile there was added 4 ml of 37% aqueous formaldehyde and then 1 g of NaBH$_3$CN. Stirring was carried out for 30 minutes at room temperature and addition was then made of glacial acetic acid to neutrality. The mixture was stirred for 3 hours at room temperature. The solvent was removed under vacuum, the residue made alkaline and extracted with chloroform. The chloroform was washed with water to neutrality, the whole was dried and evaporated under reduced pressure. The remained oil was taken up with ethanol to which was added 2 ml of 18% alcoholic HCl. Dilution with ethyl ether caused precipitation of 2.67 g of 2-[$\alpha$-(2-N,N-dimethylamino-phenoxy)-benzyl]-4-methyl-morpholine monohydrochloride (yield 74%).

I.R. $\nu$max (CHCl$_3$) 2700 cm$^{-1}$ (NH+).

EXAMPLE 52

To a solution of 6.5 g of 2-[$\alpha$-(2-nitro-phenoxy)-benzyl]-4-methylmorpholine in 200 ml of absolute EtOH there was added 0.7 g of Palladium-charcoal (5%) and the mixture was hydrogenated at 2.5 atm. for 0.5 hours. The catalyst was filtered out, the solution evaporated to dryness and the residual oil was converted to hydrochloride with alcoholic HCl. Crystallization from EtOAc/EtOH, gave 5.1 g of 2-[$\alpha$-(2-amino-phenoxy)-benzyl]-4-methyl-morpholine mono hydrochloride. Yield 76%.

I.R. $\nu$max (KBr) 3400 cm$^{-1}$ (NH$_2$); 2700 cm$^{-1}$ (NH+).

EXAMPLE 53

To a solution of 4.5 g of 2-[$\alpha$-(2-hydroxy-phenoxy)-benzyl]-4-methylmorpholine in 70 ml of anhydrous DMF there was added 2.2 g of K$_2$CO$_2$ and, at room temperature, slow dropwise addition was made of 1 ml of CH$_3$I. After the addition, stirring was carried out for 5 hours at 55° C. The mixture was poured into 700 ml of cold water and extracted with ethyl ether. After washing with NaCl-saturated H$_2$O and dehydration with sodium sulphate, the ether extracts were concentrated to a small volume. To the residue there was added 18% alcoholic HCl to obtain 4 g of 2-[$\alpha$-(2-methoxy-phenoxy)-benzyl]-4-methyl-morpholine hydrochloride, m.p. 67°–90° C. (dec.) (yield 76%).

I.R. $\nu$ max (KBr) 2820 cm$^{-1}$ (OCH$_3$); 2700 cm$^{-1}$ (NH+).

EXAMPLE 54

To a solution of 15 g of 2-[$\alpha$-(2-amino-phenoxy)-benzyl]-4-methylmorpholine hydrochloride in 50 ml of water there was added 18.5 ml of 23% HCl. The mixture was cooled to 0° C. and to it there was then slowly added, under stirring, a solution of 3.45 g of sodium nitrite in 20 ml of water. After 20 minutes, the temperature was allowed to rise to room temperature. The whole was heated in a water bath at 40° C. until nitrogen no longer evolved. Extraction was performed with chloroform after adjusting the pH to 9. The organic extracts were dried, and evaporated to dryness and the residue was dissolved in 5 ml of absolute ethanol. There was added 9 ml of 20% ethanolic HCl. On dilution with a small quantity of ethyl ether there precipitated 2-[$\alpha$-(2-hydroxyphenoxy)-benzyl]-4-methyl-morpholine hydrochloride (4.65 g). Yield 31%.

I.R. $\nu$ max (KBr) 3500 cm$^{-1}$ (OH); 2700 cm$^{-1}$ (NH+).

EXAMPLE 55

To 5.1 g of 2-[$\alpha$-(2-nitro-phenoxy)-benzyl]-4-methyl-morpholine dissolved in 70 ml of anhydrous toluene there was added 3 ml of ethyl chlorocarbonate and the mixture was refluxed for 24 hours. Then it was evaporated to dryness and there was obtained 5.9 g of oil which was taken up with 15 ml of 8% alcoholic aqueous HCl and refluxed for 4 hours. After evaporation to dryness, the residue was taken up with 50 ml of H$_2$O and extraction performed with ethyl ether. After washing with a saturated solution of NaCl and dehydration with sodium sulphate, the ether extracts were concentrated to a small volume. By adding alcoholic HCl (18% in absolute EtOH) there was caused to precipitate 3.5 g of 2-[$\alpha$-(2-nitro-phenoxy)-benzyl]-morpholine hydrochloride. Yield 68%.

I.R. ν max 2800 cm$^{-1}$ (NH); 1525 cm$^{-1}$ (NO$_2$).

The compounds of Example 20 were similarly prepared.

EXAMPLE 56

A solution of 4-benzyl-2-[α-(2-methoxy-phenoxy)-benzyl]-morpholine (5 g) in 99% EtOH (150 ml) and HCl (6 ml) was reduced (palladium-charcoal catalyst) for 4 hours at room temperature. The mixture was then filtered, dried under vacuum and separated on a silica gel column (mobile phase: CHCl$_3$:MeOH:N-H$_4$OH=170:30:2) to obtain 2-[α-(2-methoxy-phenoxy)-benzyl]-morpholine (2.1 g; yield 54.7%) as a transparent oil. HCl m.p. 140°–170° C.

The morpholine derivatives mentioned in the Example 20 except those containing nitro or chloro were analogously prepared.

EXAMPLE 57

A solution of 4-benzyl-2-[α-(2-methoxy-phenoxy)-benzyl]morpholine (5 g) in benzene (70 ml) with ethyl chloroformate (1.23 ml) was refluxed for 5 hours. The solvent was evaporated and the residue was heated at reflux for 2 days with 10% KOH (70 ml) in MeOH solution. The whole was evaporated to dryness and the residue was partitioned between ethyl ether and water.

The water was extracted with fresh ether. An acid-base purification was performed using ether as extraction solvent. Dry over Na$_2$SO$_4$, filtration and evaporation under vacuum gave 2-[α-(2-methoxy-phenoxy)-benzyl]-morpholine (2.4 g: yield 60%)-as a mixture of the diastereoisomers .HCl m.p. 140°–170° C. All the compounds listed in Example 20 were similarly prepared.

EXAMPLE 58

To a solution of 1.23 g of LiAlH$_4$ in 50 ml of Et$_2$O dropwise addition was made of 6.8 g of 4-benzyl-[α-(2-methoxy-phenoxy)-benzyl]-morpholin-5-one dissolved in 100 ml of anhydrous Et$_2$O and 30 ml of anhydrous tetrahydrofuran. The reaction mixture was stirred for two days at room temperature and then quenched with H$_2$O/NaOH/H$_2$O and filtered; the solid was washed with hot tetrahydrofuran and the filtrate dried over Na$_2$SO$_4$ and then brought to complete dryness under vacuum, in this way obtaining 4-benzyl-2-[α-(2-methoxy-phenoxy)-benzyl]-morpholine (4.9 g; yield 78%) as a transparent oil.

Analogously, the 4-benzyl-2-[α-(2-ethoxy-phenoxy)-benzyl]morpholine as well as the compounds of the Examples 17, 19 and 20, except those containing chloro, were prepared.

EXAMPLE 59

To a solution of N-benzylamino-2-hydroxy-3-(2-methoxy-phenoxy)-3-phenyl-propylamine (3.5 g) in CH$_2$Cl$_2$ (60 ml), NaOH (0.6 g) and water (16 ml) were added at 0° C. The whole was cooled to −50° C. and chloroacetyl chloride (1.1 ml) diluted in CH$_2$Cl$_2$ (10 ml) was added dropwise. The organic extracts were combined and washed with a saturated solution of NaCl, drying was carried out over Na$_2$SO$_4$ and the solution was then evaporated to dryness, so obtaining N-benzyl-N-chloroacetyl-2-hydroxy-3-(2-methoxy-phenoxy)-3-phenylpropylamine (4.0 g; yield 93%) as an oil, chromatographically pure, which is used as such.

2.5 g of this product was dissolved in dimethyl sulphoxide (10 ml) then 55% NaH (0.275 g) was added; after 1.5 hours at room temperature the whole was poured into water and extracted with EtOAc.

The organic extract was washed several times with water, dried over Na$_2$SO$_4$ and evaporated to dryness, so obtaining 4-benzyl-2-[α-(2-methoxy-phenoxy)-benzyl]-morpholin-5-one (2.2 g; yield 94%).

The 4-benzyl-2-[α-(2-ethoxy-phenoxy)-benzyl]-morpholin-5-one as well as the 4-benzyl-derivatives useful for the preparation of the compounds of Example 20, according to the procedure of Examples 56 and 57, were similarly prepared.

EXAMPLE 60

(a) To a solution of 2-hydroxy-3-(2-methoxy-phenoxy)-3-phenyl-propylamine (6 g) in CH$_2$Cl$_2$ (70 ml), a solution of NaOH (1.3 g) and water (40 ml) was added dropwise. Dropwise addition was then made of benzoyl chloride (3.6 ml) dissolved in CH$_2$Cl$_2$ (20 ml) at 0° C. The whole was stirred for 30 minutes, the organic layer was separated and the aqueous phase was extracted with CH$_2$Cl$_2$; the combined organic extracts were washed with a saturated aqueous solution of NaCl, dried over Na$_2$SO$_4$ and then the solution was evaporated to complete dryness, so obtaining N-benzoylamino-2-hydroxy-3-(2-methoxy-phenoxy)-3-phenyl-propylamine (8.1 g; yield 98%) as an oil.

(b) to a solution of LiAlH$_4$ (16.3 g) in anhydrous Et$_2$O (1000 ml) a solution of the oil obtained according to the process under (a) of the present example (8.1 g) in anhydrous Et$_2$O (1500 ml) was added and the whole was kept at reflux for 12 hours. After a normal processing and an acid-base purification with Et$_2$O as solvent and after evaporation to dryness, N-benzylamino-2-hydroxy-3-(2-methoxy-phenoxy)-3-phenyl-propylamine (35 g; yield 45%) was obtained as mixture of diasteroisomers (colourless oil).

Analogously, the N-benzylamino-2-hydroxy-3-(2-ethoxy-phenoxy)-3-phenyl-propylamine, as well as the N-benzylamino-derivatives useful for the preparation of the compounds of Example 59, were prepared.

EXAMPLE 61

Tablets were prepared, each weighing 200 mg and each containing 25 mg of active ingredient, in the manner described below:

Composition (for 10,000 tablets)

2-[α-(2-methoxy-phenoxy)-benzyl]-morpholine: 250 g

Lactose: 1.230 g

Corn starch: 450 g

Talc (powdered): 50 g

Magnesium stearate: 20 g

The 2-[α-(2-methoxy-phenoxy)-benzyl]-morpholine, the lactose and half of the corn starch were mixed, sieved through a 0.55 mm mesh screen. 30 g of corn starch was dispersed in 300 ml of hot water. The mixture of the powders was granulated with the starch mucilage obtained. The granulate was dried and passed through a 1.4 mm mesh screen. The rest of the starch was added, as also the talc and the magnesium stearate. A careful blending was performed and the mass was compressed into tablets with 8 mm diameter punches.

EXAMPLE 62

Tablets were prepared, each weighing 200 mg and each containing 25 mg of active ingredient:

Composition (for 10,000 tablets)

N-methyl-2-methoxy-3-(2-ethoxy-phenoxy)-3-phenyl-propylamine: 250 g

Lactose: 1.230 g
Corn starch: 450 g
Talc (powdered): 50 g
Magnesium stearate: 20 g
The tablets were prepared as described in Example 61.
We claim:
1. A compound having the following formula (I)

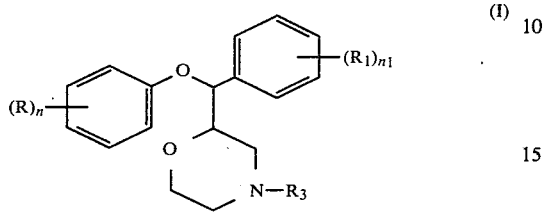

wherein
n and $n_1$ are, independently, 1, 2 or 3;
one or more of the groups R and $R_1$, which may be the same or different, is $-NO_2$ or

wherein $R_5$ and $R_6$ are, independently, hydrogen or $C_1-C_6$ alkyl, or two adjacent R groups or two adjacent $R_1$ groups, taken together, form the $-O-CH_2-O-$ radical; and the remainder of the groups R and $R_1$ are hydrogen;
$R_3$ is (a') hydrogen; (b') $C_1-C_6$ alkyl unsubstituted or substituted by one or more substituents chosen from the group consisting of halogen, hydroxy, $C_1-C_6$ alkoxy,

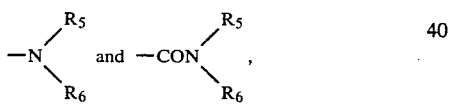

where $R_5$ and $R_6$ are as defined above; (c') $C_2-C_4$ alkenyl; $C_2-C_4$ alkynyl; (d') phenyl-$C_1-C_4$ alkyl, in which the phenyl group may be unsubstituted or substituted by one or more substituents chosen from the group consisting of $C_1-C_6$ alkyl, halogen, halo-$C_1-C_6$ alkyl, hydroxy, $C_1-C_6$ alkoxy, and

wherein $R_5$ and $R_6$ are as defined above; (e') $C_3-C_7$ cycloalkyl unsubstituted or substituted by one or more $C_1-C_6$ alkyl, halogen, halo-$C_1-C_6$ alkyl, hydroxy, $C_1-Chd 6$ alkoxy and

where $R_5$ and $R_6$ are as defined above;
and the pharmaceutically acceptable salts thereof.

2. A compound having the following formula (I)

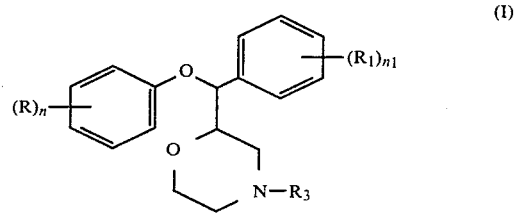

wherein
n and $n_1$ are, indpendently, 1, 2 or 3;
two adjacent R groups or two adjacent $R_1$ groups, taken together, form the $-O-CH_2-O-$ radical, and the other groups R and $R_1$ are hydrogen; $R_3$ is (a') hydrogen; (b') $C_1-C_6$ alkyl unsubstituted or substituted by one or more substituents chosen from the group consisting of halogen, hydroxy, $C_1-C_6$ alkoxy,

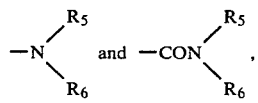

where $R_5$ and $R_6$ are as defined above; (c') $C_2-C_4$ alkenyl; $C_2-C_4$ alkynyl; (d') phenyl-$C_1-C_4$ alkyl, in which the phenyl group may be unsubstituted or substituted by one or more substituents chosen from the group consisting of $C_1-C_6$ alkyl, halogen, halo-$C_1-C_6$ alkyl, hydroxy, $C_1-C_6$ alkoxy, and

where $R_5$ and $R_6$ are as defined above; (e') $C_3-C_7$ cycloalkyl unsubstituted or substituted by one or more $C_1-C_6$ alkyl, halogen, halo-$C_1-C_6$ alkyl, hydroxy, $C_1-C_6$ alkoxy and

where $R_5$ and $R_6$ are as defined above;
and the pharmaceutically acceptable salts thereof.

3. A compound having the following formula (I)

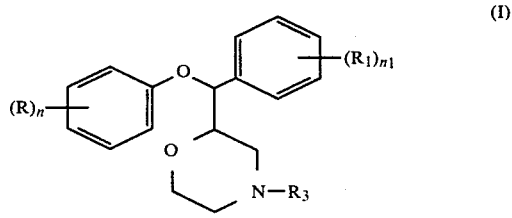

wherein
n and $n_1$ are, independently, 1, 2 or 3;

two adjacent R groups or two adjacent $R_1$ groups, taken together, form the —O—CH$_2$—O— radical, and the other groups R and $R_1$ are hydrogen;

$R_3$ is hydrogen, methyl or isopropyl;

and the pharmaceutically acceptable salts thereof.

4. 2-[α-(3,4-methylendioxy-phenoxy)-benzyl]-morpholine and the pharmaceutically acceptable salts thereof.

5. A salt of the compound of claim 3 wherein the salt is the hydrochloride.

6. A compound having the following formula (I)

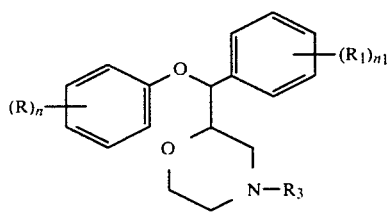

wherein n and $n_1$ are, independently, 1, 2 or 3;

one or more of the groups R and $R_1$, which may be the same or different, is —NO$_2$ or

wherein $R_5$ and $R_6$ are, independently, hydrogen or $C_1$–$C_6$ alkyl, and the remainder of the groups R and $R_1$ are hydrogen; $R_3$ is (a') hydrogen; (b') $C_1$–$C_6$ alkyl unsubstituted or substituted by one or more substituents chosen from the group consisting of halogen, hydroxy, $C_1$–$C_6$ alkoxy,

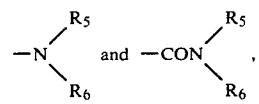

where $R_5$ and $R_6$ are as defined above; (c') $C_2$–$C_4$ alkenyl; $C_2$–$C_4$ alkynyl; (d') phenyl-$C_1$–$C_4$ alkyl, in which the phenyl group may be unsubstituted or substituted by one or more substituents chosen from the group consisting of $C_1$–$C_6$ alkyl, halogen, halo-$C_1$–$C_6$ alkyl, hydroxy, $C_1$–$C_6$ alkoxy, and

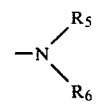

where $R_5$ and $R_6$ are as defined above; (e') $C_3$–$C_7$ cycloalkyl unsubstituted or substituted by one or more $C_1$–$C_6$ alkyl, halogen, halo-$C_1$–$C_6$ alkyl, hydroxy, $C_1$–$C_6$ alkoxy and

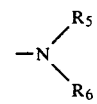

where $R_5$ and $R_6$ are as defined above;

and the pharmaceutically acceptable salts thereof.

7. A compound selected from the group consisting of:

2-[α-(2-N,N-dimethylamino-phenoxy)-benzyl]-4-methyl-morpholine;

2-[α-(2-amino-phenoxy)-benzyl]-4-methyl-morpholine;

2-[α-(2-nitro-phenoxy)-benzyl]-morpholine, and the pharmaceutically acceptable salts thereof.

8. An antidepressant composition comprising an antidepressant effective amount of a compound according to any one of claims 1–7 and a pharmaceutically acceptable carrier and/or diluent.

* * * * *